(12) United States Patent
Galvin

(10) Patent No.: US 10,604,545 B2
(45) Date of Patent: Mar. 31, 2020

(54) METHODS FOR THE PREPARATION OF OBETICHOLIC ACID AND DERIVATIVES THEREOF

(71) Applicant: Intercept Pharmaceutical, Inc., New York, NY (US)

(72) Inventor: Gabriel M Galvin, San Diego, CA (US)

(73) Assignee: INTERCEPT PHARMACEUTICALS, INC., New York, NY (US)

(*) Notice: Subject to any disclaimer, the term of this patent is extended or adjusted under 35 U.S.C. 154(b) by 0 days.

(21) Appl. No.: 15/773,620

(22) PCT Filed: Oct. 28, 2016

(86) PCT No.: PCT/US2016/059440
§ 371 (c)(1),
(2) Date: May 4, 2018

(87) PCT Pub. No.: WO2017/079062
PCT Pub. Date: May 11, 2017

(65) Prior Publication Data
US 2019/0062367 A1 Feb. 28, 2019

Related U.S. Application Data

(60) Provisional application No. 62/252,077, filed on Nov. 6, 2015.

(51) Int. Cl.
| | | |
|---|---|---|
| C07J 9/00 | (2006.01) | |
| C07J 17/00 | (2006.01) | |
| C07J 31/00 | (2006.01) | |
| C07J 41/00 | (2006.01) | |
| C07J 43/00 | (2006.01) | |

(52) U.S. Cl.
CPC .............. *C07J 9/005* (2013.01); *C07J 9/00* (2013.01); *C07J 17/00* (2013.01); *C07J 31/006* (2013.01); *C07J 41/0061* (2013.01); *C07J 43/003* (2013.01)

(58) Field of Classification Search
CPC . C07J 9/005; C07J 9/00; C07J 41/0061; C07J 17/00; C07J 31/006; C07J 43/003
See application file for complete search history.

(56) References Cited

U.S. PATENT DOCUMENTS

| | | |
|---|---|---|
| 10,149,921 B2 | 12/2018 | Jin et al. |
| 2009/0062526 A1 | 3/2009 | Yu et al. |
| 2013/0345188 A1 | 12/2013 | Steiner et al. |
| 2015/0291653 A1 | 10/2015 | Pellicciari et al. |

FOREIGN PATENT DOCUMENTS

| | | | |
|---|---|---|---|
| CN | 104 876 995 | 9/2015 | |
| WO | WO 2002/072598 A1 | 9/2002 | |
| WO | WO 2006/122977 A2 | 11/2006 | |
| WO | WO 2013/192097 A1 | 12/2013 | |
| WO | WO-2014066819 A1 * | 5/2014 | ............... C07J 9/00 |

OTHER PUBLICATIONS

Pellicciari et al (Journal of Medicinal Chemistry, 6a-Ethyl-Chenodeoxycholic Acid (6-ECDCA), a Potent and Selective FXR Agonist Endowed with Anticholestatic Activity, 2002, 45(17), pp. 3569-3572. (Year: 2002).*

Zaragoza Dorwald, Side Reactions in Organic Synthesis, 2005, WILEY-VCH Verlag GmbH & Co. KGaA, Weinheim, Preface. p. IX . (Year: 2005).*

Greene, Protective Groups in Organic Synthesis, 1981, John Wiley & Sons, Inc., New York, p. 40-43. (Year: 1981).*

Yu, D. et al, "An improved synthesis of 6α-ethylchenodeoxycholic acid (6ECDCA), a potent and selective agonist for the Farnesoid X Receptor (FXR)", Steroids, 2012, vol. 77, pp. 1335-1338.

Yu, D. et al. "Novel FXR (farnesoid X receptor) modulators: Potential therapies for cholesterol gallstone disease", Bioorganic & Medicinal Chemistry, vol. 24, No. 18, 2016, pp. 3986-3993.

* cited by examiner

*Primary Examiner* — Paul A Zucker
(74) *Attorney, Agent, or Firm* — Michelle Iwamoto-Fan

(57) ABSTRACT

The present application relates to a method of preparing a bile acid derivative or a pharmaceutical acceptable salt, solvate, or amino acid conjugate thereof, comprising direct alkylation of a carbon atom at the C-6 position of 7 keto lithocholic acid (KLCA) with an alkylating agent and reduction of a keto group at the C-7 position.

16 Claims, No Drawings

METHODS FOR THE PREPARATION OF OBETICHOLIC ACID AND DERIVATIVES THEREOF

BACKGROUND

Farnesoid X receptor (FXR) is a nuclear receptor that functions as a bile acid sensor controlling bile acid homeostasis. FXR is expressed in various organs and shown to be involved in the regulation of many diseases and conditions, such as liver diseases, lung diseases, renal diseases, intestinal diseases, and heart diseases, and biological processes, including glucose metabolism, insulin metabolism, and lipid metabolism.

Numerous bile acid derivatives are FXR agonists, and are able to regulate FXR-mediated diseases and conditions. Obeticholic acid (i.e., OCA, 6-ethylchenodeoxycholic acid, or 6-ECDCA) possesses potent FXR agonistic activity. Various methods of synthesizing OCA have been described, for example, in WO2002/072598, WO2006/122977, and more recently WO2013/192097. However, there are still needs for improved processes that are capable of preparing OCA and derivatives thereof with an increased yield; reduced cost, and good safety profile. The present application addresses such needs.

SUMMARY

The present application relates to methods of preparing obeticholic acid (OCA) and derivatives thereof. In one aspect, the present application relates to a method of preparing obeticholic acid (OCA):

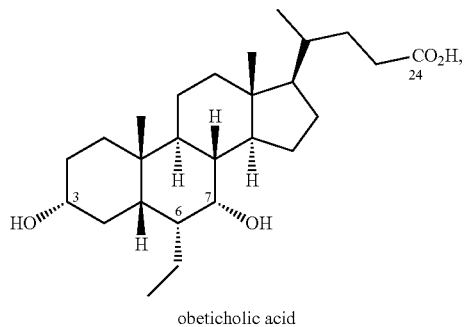

obeticholic acid or a pharmaceutical acceptable salt, solvate, or amino acid conjugate thereof through direct alkylation at the C-6 position.

Specifically, the present application relates to a method of preparing OCA, or a pharmaceutical acceptable salt, solvate, or amino acid conjugate thereof, comprising alkylating the carbon atom at the C-6 position of Compound 1 with an alkylating agent to form Compound 2:

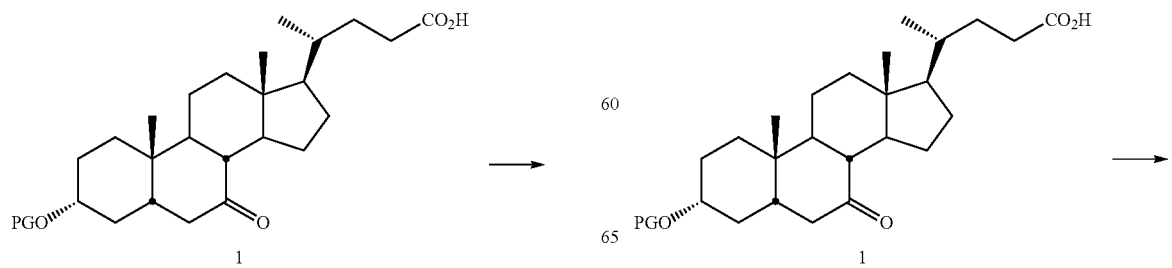

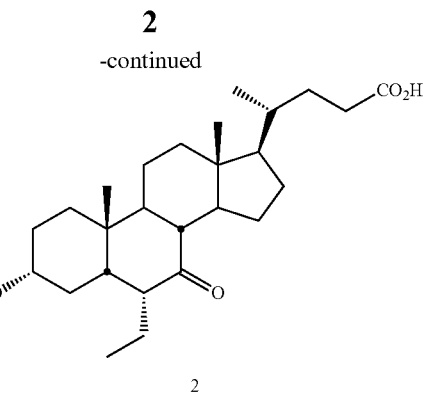

wherein PG is a protecting group, and reducing the keto group at the C-7 position of Compound 2 to form OCA:

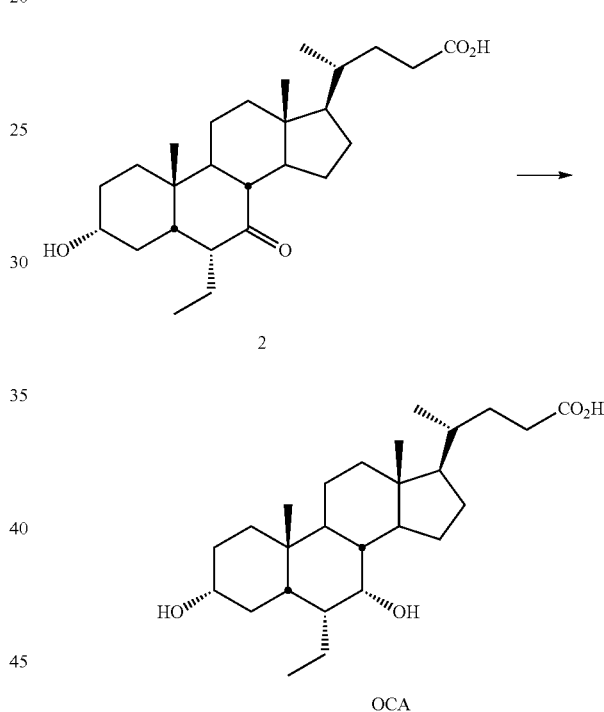

The present application also relates to a method of preparing Compound 2, or a pharmaceutical acceptable salt, solvate, or amino acid conjugate thereof, comprising alkylating the carbon atom at the C-6 position of Compound 1 with an alkylating agent to form Compound 2:

3
-continued

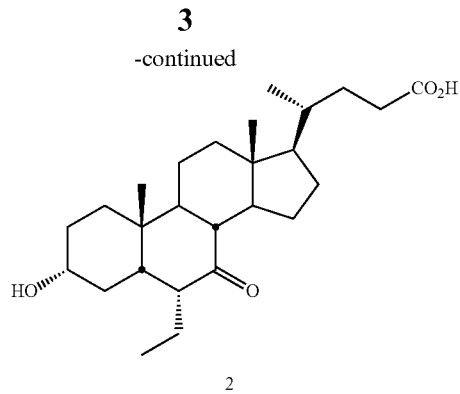
2 wherein PG is a protecting group.

The present application also relates to a method of preparing Compound 2, or a pharmaceutical acceptable salt, solvate, or amino acid conjugate thereof, comprising:

protecting the hydroxyl group at the C-3 position of KLCA to form Compound 1:

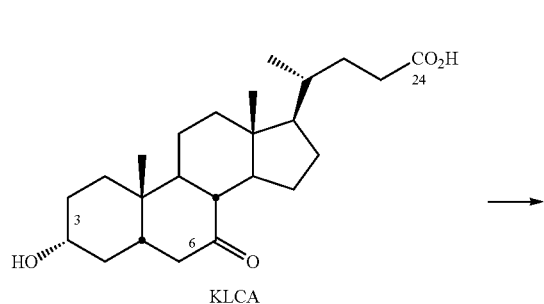
KLCA

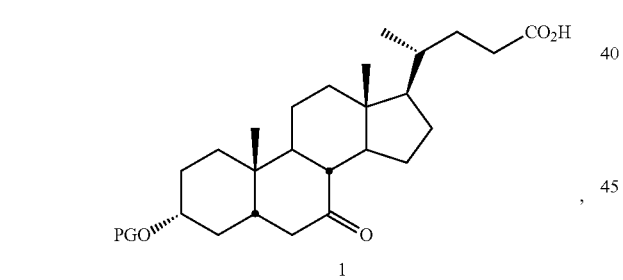
1 wherein PG is a protecting group, and alkylating the carbon atom at the C-6 position of Compound 1 with an alkylating agent to form Compound 2:

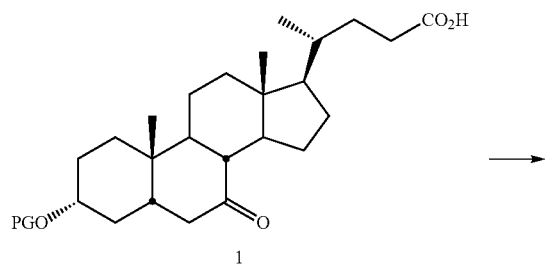
1

4
-continued

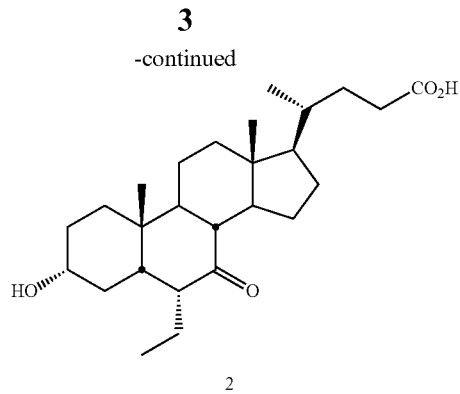
2

The present application also relates to a method of preparing OCA, or a pharmaceutical acceptable salt, solvate, or amino acid conjugate thereof, comprising:

protecting the hydroxyl group at the C-3 position of KLCA to form Compound 1:

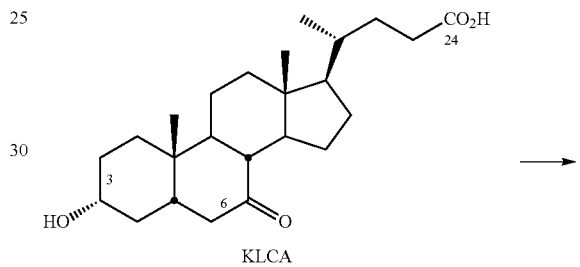
KLCA

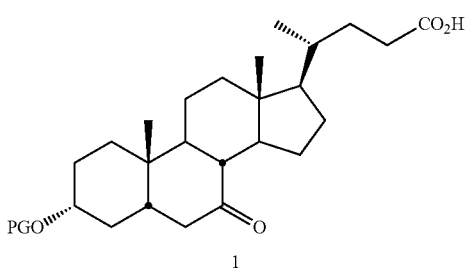
1 wherein PG is a protecting group, alkylating the carbon atom at the C-6 position of Compound 1 with an alkylating agent to form Compound 2:

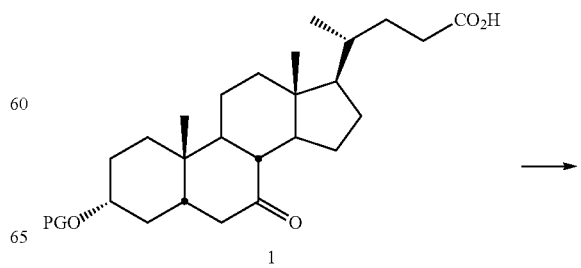
1

-continued

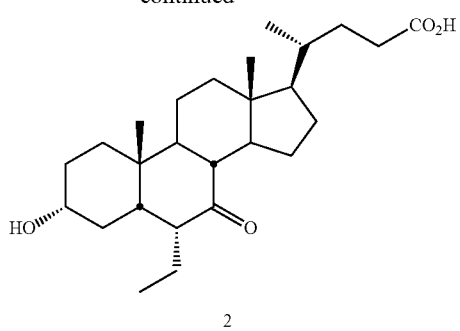

2 and
reducing the keto group at the C-7 position of Compound 2 to form OCA:

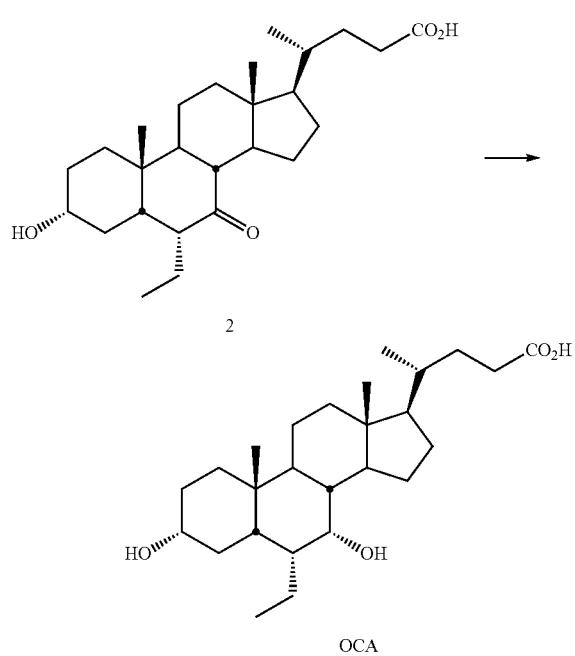

The present application also relates to a method of preparing 6α-ethyl-act, 7α-23-trihydroxy-24-nor-5β-cholan-23-sulfate (Compound 9):

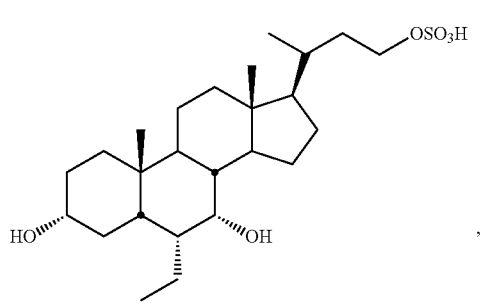

9 or a pharmaceutical acceptable salt, solvate, or amino acid conjugate thereof, comprising:

esterifying OCA to form Compound 4:

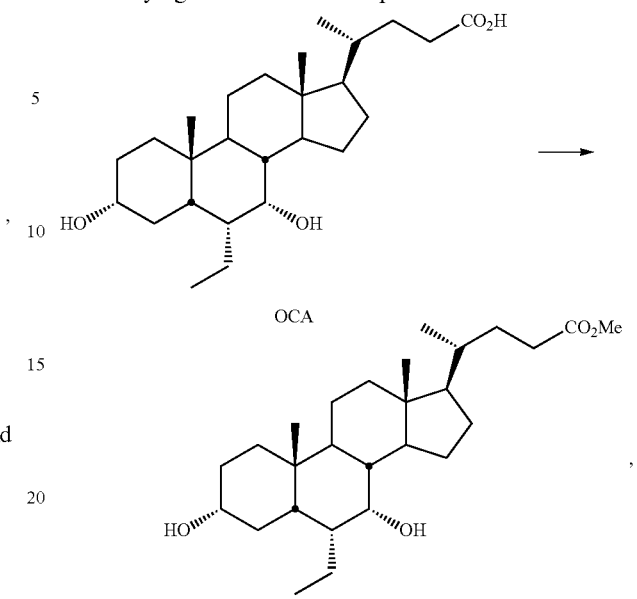

converting Compound 4 to form Compound 5:

converting Compound 5 to form Compound 6:

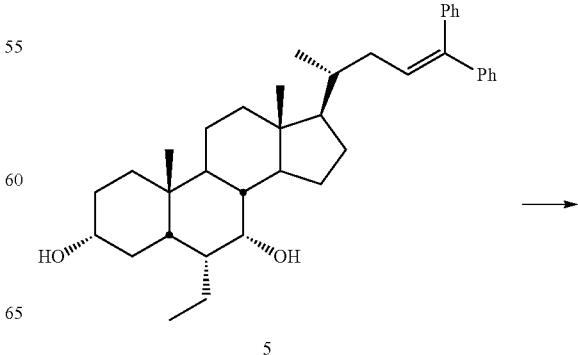

7

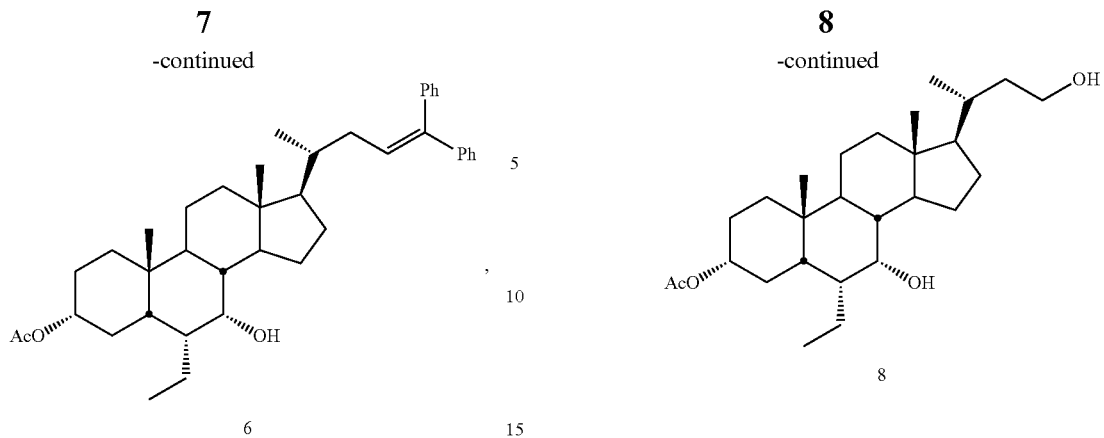

converting Compound 6 to form Compound 7:

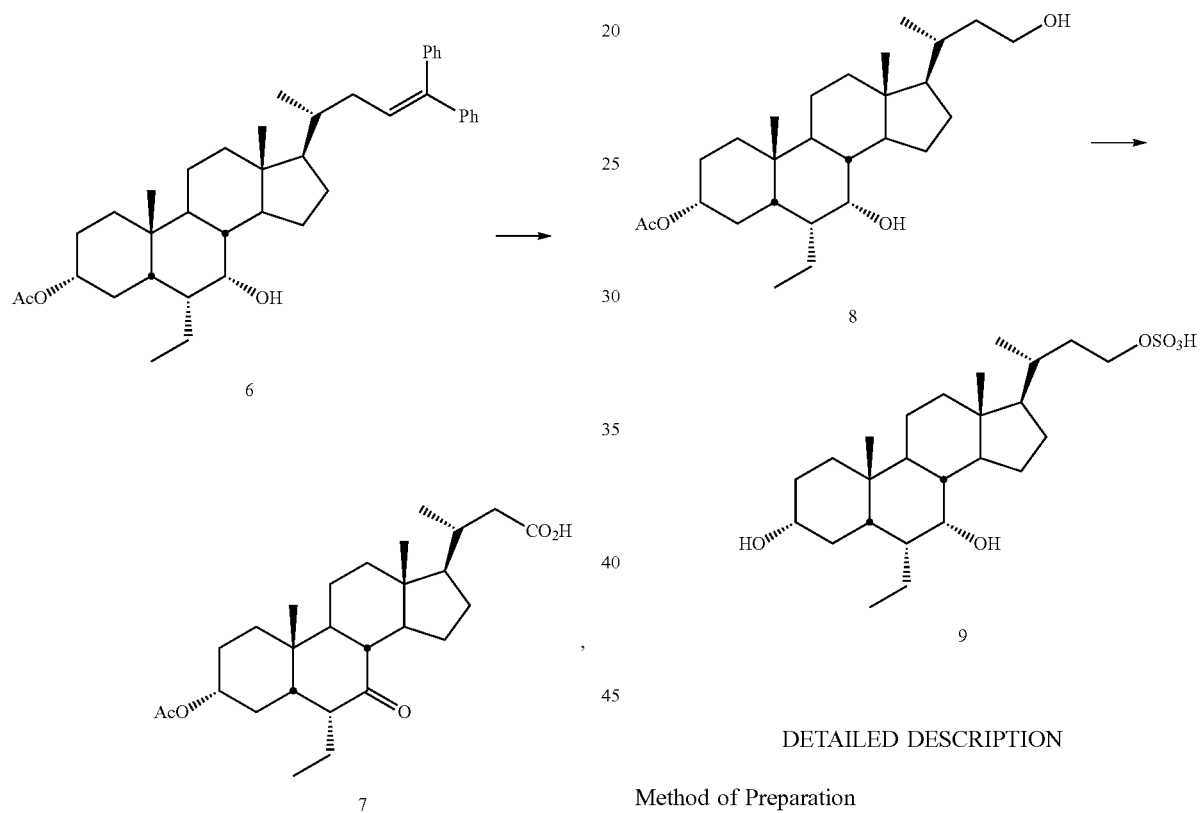

converting Compound 7 to form Compound 8:

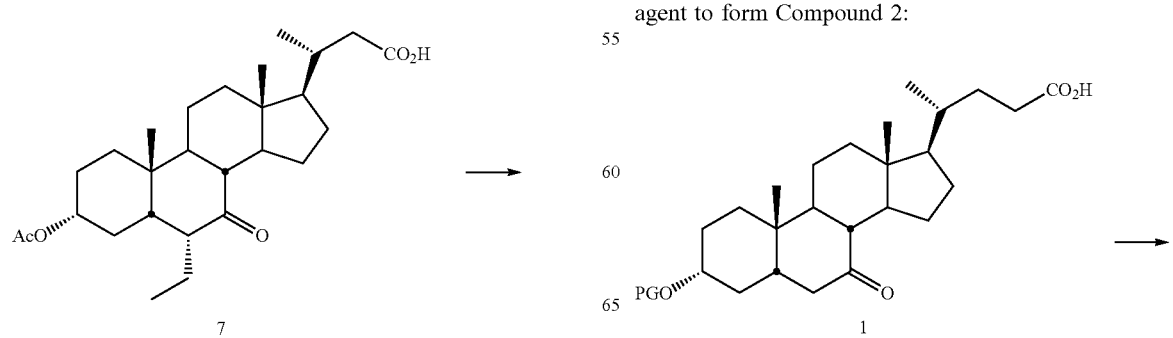

8 and converting Compound 8 to form Compound 9:

DETAILED DESCRIPTION

Method of Preparation

The present application provides a method of preparing OCA, or a pharmaceutical acceptable salt, solvate, or amino acid conjugate thereof, comprising alkylating the carbon atom at the C-6 position of Compound 1 with an alkylating agent to form Compound 2:

-continued

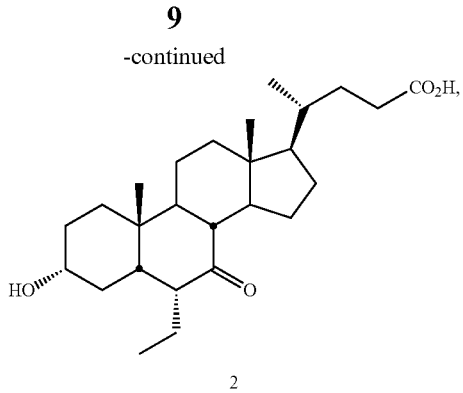

2 wherein PG is a protecting group, and
reducing the keto group at the C-7 position of Compound 2 to form OCA:

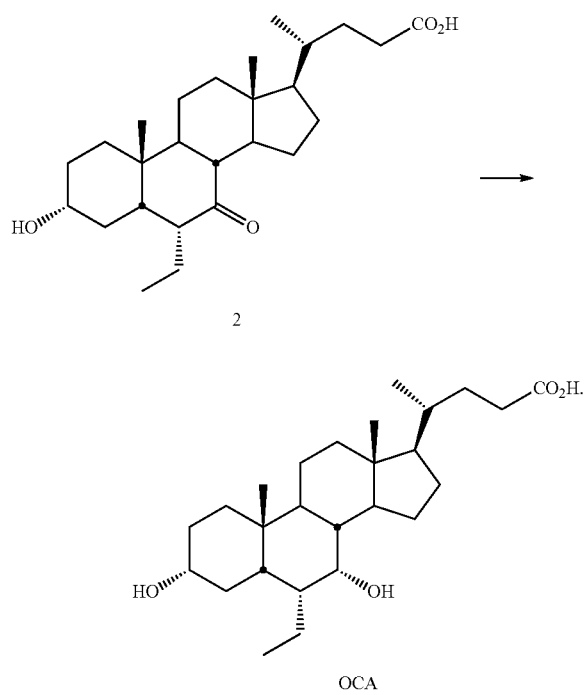

The present application also relates to a method of preparing Compound 2, or a pharmaceutical acceptable salt, solvate, or amino acid conjugate thereof, comprising alkylating the carbon atom at the C-6 position of Compound 1 with an alkylating agent to form Compound 2:

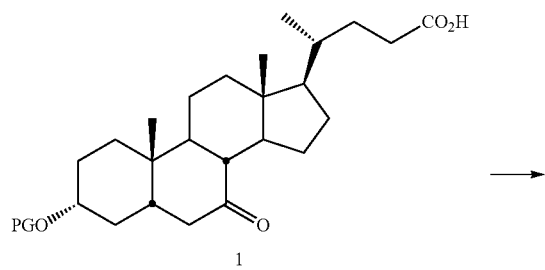

-continued

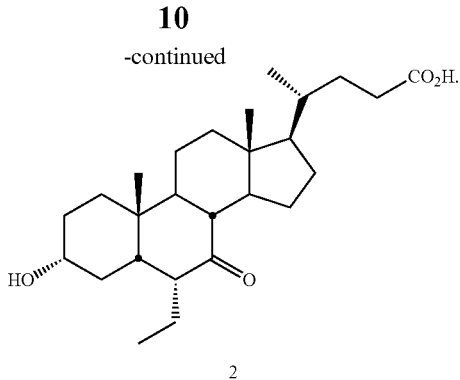

2

In one embodiment, the alkylating agent is selected from alkyl halide (e.g., ethyl halide), alkyl tosylate (e.g., ethyl tosylate), alkyl mesylate (e.g., ethyl mesylate), sulfonate ester (e.g., sulfonate ethyl ester), alkyl oxonium salt (e.g., $Et_3O.BF_4$), dialkyl sulfate (e.g., diethyl sulfate), dialkyl carbonate (e.g., diethyl carbonate), and tetraalkylammonium salt (e.g., tetraethylammonium salt). In one embodiment, the alkylating agent is alkyl halide. In one embodiment, the alkylating agent is ethyl halide (Et-X), wherein Et is ethyl and X is halogen (e.g., F, Cl, Br, or I). In one embodiment, the alkyl halide is ethyl bromide or ethyl iodide. In one embodiment, the alkyl halide is ethyl bromide. In one embodiment, the alkylation is conducted in an aprotic solvent. In one embodiment, the aprotic solvent is selected from tetrahydrofuran (THF), ethyl acetate (EtOAc), acetone, dimethylformamide (DMF), acetonitrile (MeCN), dimethyl sulfoxide (DMSO), toluene, hexane, benzene, 1,4-dioxane, chloroform, dichloromethane (DCM), diethyl ether, and methyl tert-butyl ether (MTBE). In one embodiment, the aprotic solvent is selected from THF, MTBE, toluene, and DMF.

In one embodiment, the alkylation is conducted in the presence of a deprotonating agent. In one embodiment, the deprotonating agent is selected from $C_1$-$C_6$ alkoxide (e.g., methoxide, ethoxide, propoxide, iso-propoxide, butoxide, iso-butoxide, tort-butoxide, pentoxide, iso-pentoxide, tert-pentoxide, and hexyloxide), metal hydroxide, and metal hydride. In one embodiment, the deprotonating agent is metal $C_1$-$C_6$ alkoxide, such as sodium tert-butoxide, potassium tert-butoxide, sodium tert-pentoxide, and potassium ten-pentoxide. In one embodiment, the deprotonating agent is a metal hydroxide, such as sodium hydroxide and potassium hydroxide. In one embodiment, the deprotonating agent is a metal hydride, such as sodium hydride and potassium hydride. One skilled in the art will recognize which metal hydride functions as a deprotonating agent instead of a reducing agent.

In one embodiment, the deprotonating agent is LDA. In one embodiment, a solution of Compound 1 is charged to a solution comprising LDA at a temperature<–30° C. In one embodiment, the solution comprising Compound 1 and LDA is charged to a solution comprising an alkylating agent. In one embodiment, the alkylating agent in the solution is selected from alkyl halide (e.g., ethyl halide), alkyl tosylate (e.g., ethyl tosylate), alkyl mesylate (e.g., ethyl mesylate), sulfonate ester (e.g., sulfonate ethyl ester), alkyl oxonium salt (e.g., $Et_3O.BF_4$), dialkyl sulfate (e.g., diethyl sulfate), dialkyl carbonate (e.g., diethyl carbonate), and tetraalkylammonium salt (e.g., tetraethylammonium salt).

In one embodiment, the method further comprises deprotonating Compound 1 before Compound 1 is alkylated. In one embodiment, Compound 1 is deprotonated at the C-6 position. In one embodiment, Compound 1 is deprotonated by a base. In one embodiment, the deprotonating agent is selected from $C_1$-$C_6$ alkoxide (e.g., methoxide, ethoxide, propoxide, iso-propoxide, butoxide, iso-butoxide, tert-butoxide, pentoxide, iso-pentoxide, tert-pentoxide, and hexyloxide), metal hydroxide, and metal hydride. In one embodiment, the deprotonating agent is metal $C_1$-$C_6$ alkoxide, such as sodium tert-butoxide, potassium tert-butoxide, sodium tert-pentoxide, and potassium tert-pentoxide. In one embodiment, the deprotonating agent is a metal hydroxide, such as sodium hydroxide and potassium hydroxide. In one embodiment, the deprotonating agent is a metal hydride, such as sodium hydride and potassium hydride.

In one embodiment, the method further comprises deprotecting Compound 1 after alkylation of the carbon atom at the C-6 position. In one embodiment, the method further comprises deprotecting the hydroxyl group at the C-3 position. In one embodiment, the method further comprises deprotecting the carboxylic group at the C-24 position, wherein the protecting group at the hydroxyl at the C-3 position is not tetrahydropyranyl. In one embodiment, the method further comprises deprotecting the carboxylic group at the C-24 position, wherein the protecting group at the hydroxyl at the C-3 position is not benzyl. In one embodiment, the deprotection is conducted under an acid condition or a basic condition. In one embodiment, the deprotection is conducted under an acid condition using an acid, such as RCM in one embodiment, the deprotection is conducted under a basic condition using a base, such as metal hydroxide (e.g., sodium hydroxide and potassium hydroxide) and carbonate (e.g., sodium carbonate).

In one embodiment, the method of the present application further comprises protecting the hydroxyl group at the C-3 position of KLCA to form Compound 1:

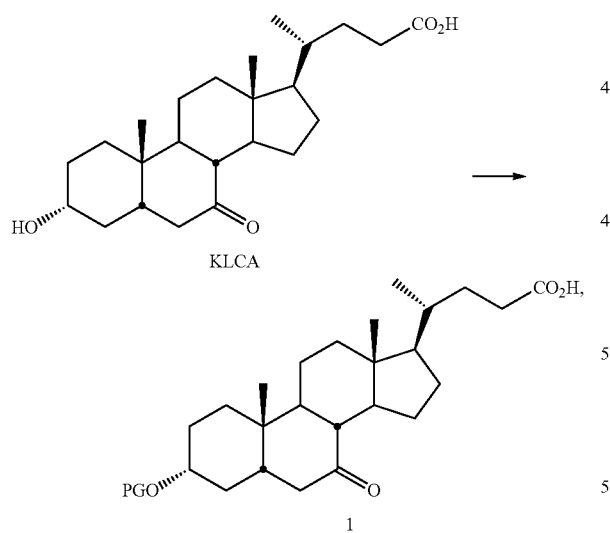

wherein PG is a protecting group.

In one embodiment, the method of the present application further comprises protecting the carboxylic group at the C-24 position in addition to the protection of the hydroxyl group at the C-3 position.

The protecting group can be any protecting group that is stable/non-reactive under the alkylation condition (e.g., non-reactive with the alkylating agent). In one embodiment, the protecting group is selected from acetyl, benzoyl, benzyl, pivaloyl, tetrahydropyranyl, tetrahydrofuranyl, 2-methoxyethoxymethyl ether (MEM), methoxymethyl ether (MOM), ethoxyethyl ether (EE), p-methoxybenzyl ether (PMB), methylthiomethyl ether, triphenylmethyl (trityl, or Tr), dimethoxytrityl (DMT), methoxytrityl (MMT), and silyl ether. In one embodiment, the silyl ether is selected from trimethylsilyl ether (TMS), triethylsilyl ether (TES), triisopropylsilyl ether (TIPS), tert-butyldimethylsilyl ether (TBDMS), and tert-butyldiphenylsilyl ether (TBDPS). In one embodiment, the protecting group is selected from TMS and TBDMS. In one embodiment, the protecting group is alkyloxycarbonyl. In one embodiment, the alkyloxycarbonyl protecting group is $C_1$-$C_6$ alkyloxycarbonyl. In one embodiment, the protecting group is optionally substituted benzyloxycarbonyl.

In another embodiment, the method of the present application further comprises removing the ester group at the C-24 position after the alkylation of the carbon atom at the C-6 position. In one embodiment, removing the ester group at the C-24 position comprises treating the ester group in a base. In one embodiment, the base is a metal hydroxide. In one embodiment, the metal hydroxide is sodium hydroxide or potassium hydroxide.

In one embodiment, the method of the present application further comprises reducing the keto group at the C-7 position of Compound 2 to form OCA:

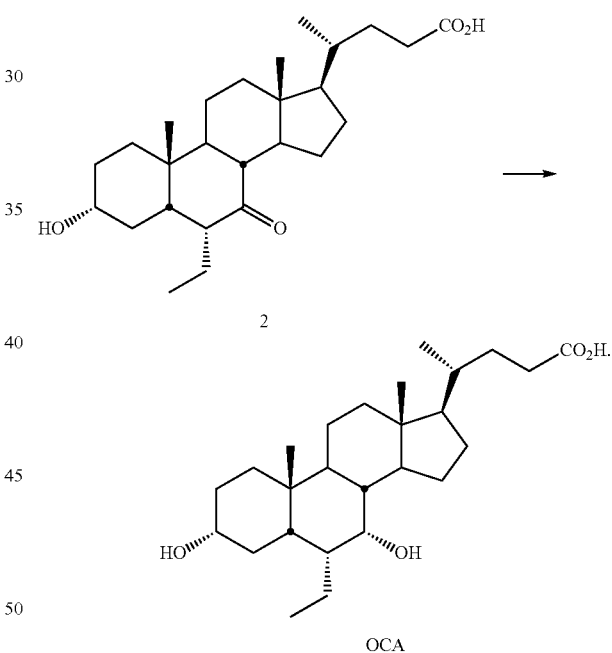

In one embodiment, the reduction comprises treating Compound 2 with a metal hydride. In one embodiment, the metal hydride is sodium borohydride or sodium triacetoxyborohydride. One skilled in the art will recognize which metal hydride functions as a reducing agent instead of a deprotonating agent.

In one embodiment, the method of the present application is conducted at a temperature above −20° C. In one embodiment, the method of the present application is conducted at a temperature between about −10° C. to about 50° C.

In one embodiment, the present application provides a method of preparing Compound 2, or a pharmaceutical acceptable salt, solvate, or amino acid conjugate thereof, comprising a) protecting the hydroxyl group at the C-3 position of KLCA to form Compound 1:

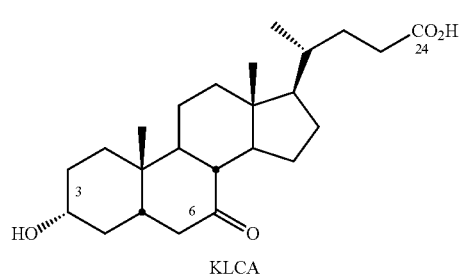

KLCA

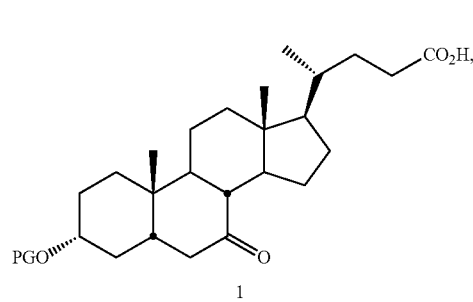

1 wherein PG is a protecting group, and b) alkylating the carbon atom at the C-6 position of Compound 1 with an alkylating agent to form Compound 2:

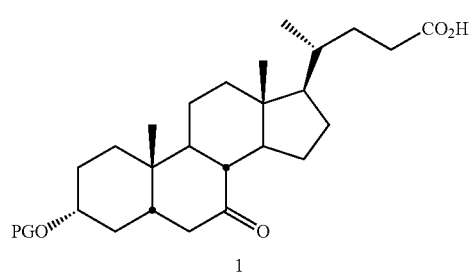

1

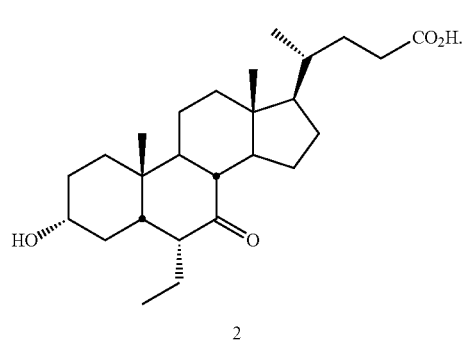

2

In one embodiment, step a) and step b) are each as described in detail above.

In one embodiment, the present application provides a method of preparing OCA, or a pharmaceutical acceptable salt, solvate, or amino acid conjugate thereof, comprising a) protecting the hydroxyl group at the C-3 position of KLCA to form Compound 1:

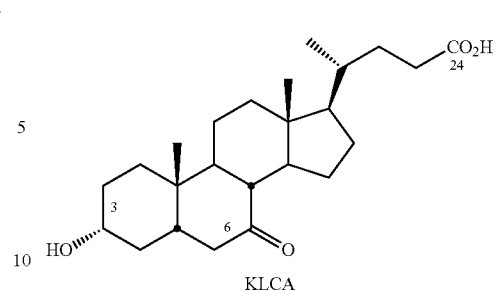

KLCA

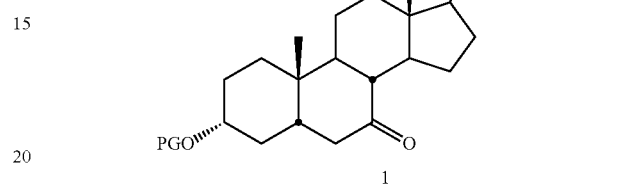

1 wherein PG is a protecting group, b) alkylating the carbon atom at the C-6 position of Compound 1 with an alkylating agent to form Compound 2:

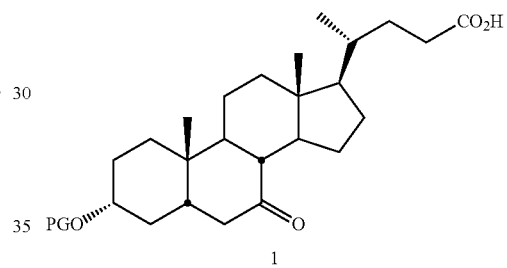

1

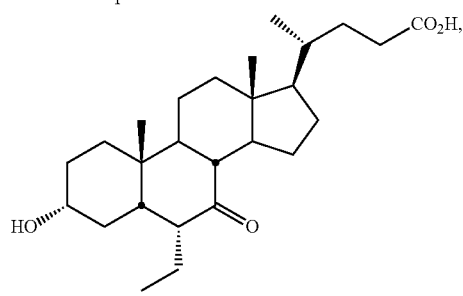

2 and c) reducing the keto group at the C-7 position of Compound 2 to form OCA:

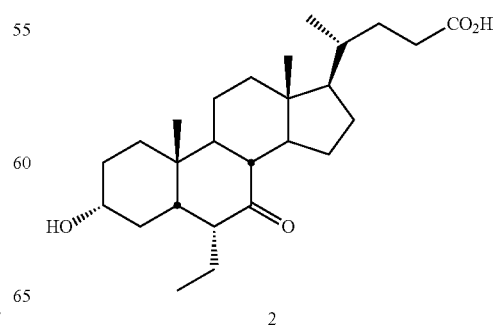

2

-continued

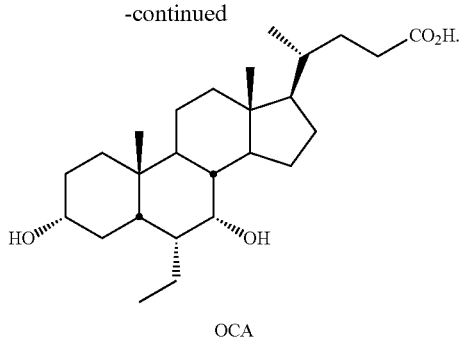

OCA

In one embodiment, step a), step b), and step c) are each as described in detail above.

In one embodiment, the method of the present application is shown in Scheme 1 below:

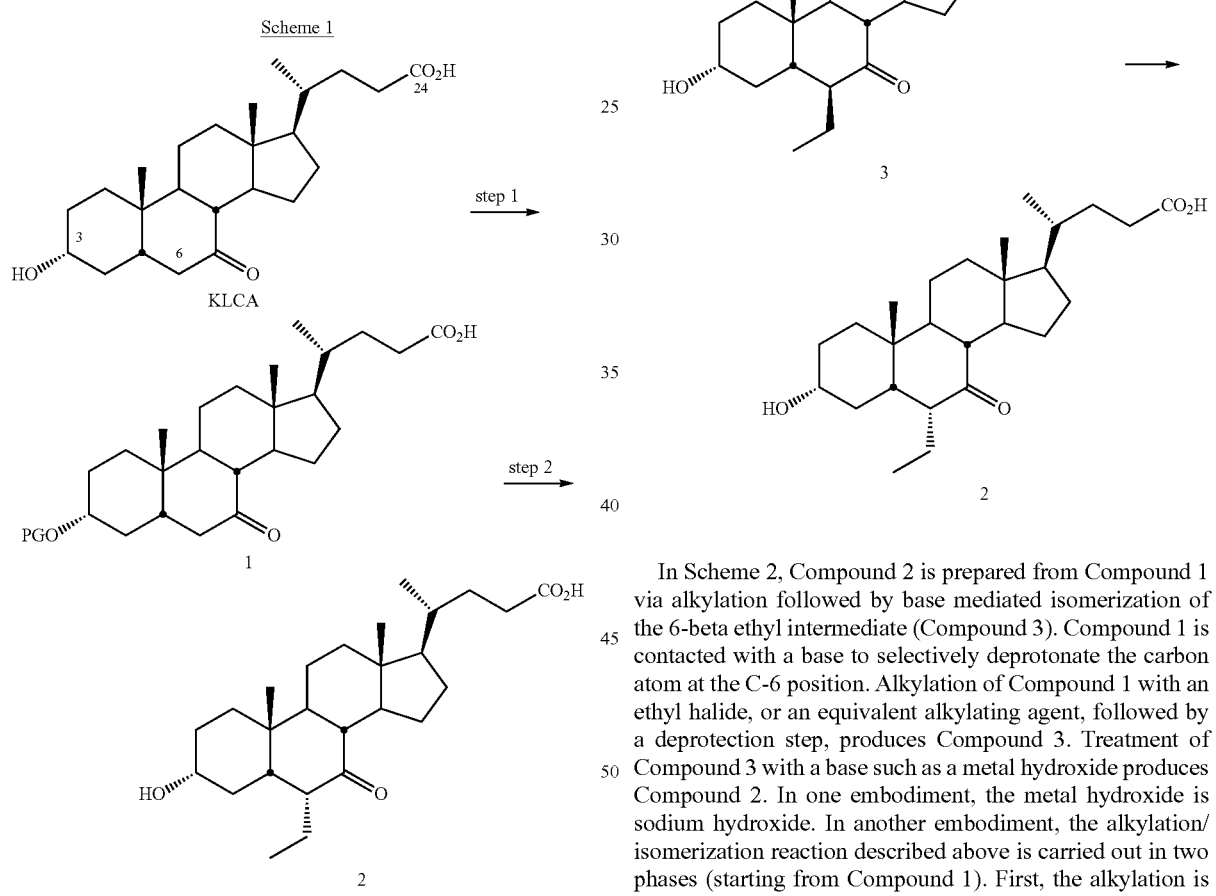

In Scheme 1, Compound 2 is prepared through a 3-step synthetic process with the starting material KLCA. The C-3 hydroxy, and optionally the C-24 carboxylic acid, in KLCA are protected with a protecting group, to form Compound 1. Compound 1 is contacted with a base (e.g., a base less reactive than lithium diisopropylamide (LDA), such as tert-butylate or an amylate salt), to selectively deprotonate the carbon atom at the C-6 position. Alkylation of Compound 1 with an ethyl halide, or an equivalent alkylating agent, followed by a deprotection step, produces Compound 2.

In one embodiment, the method of the present application is shown in Scheme 2 below:

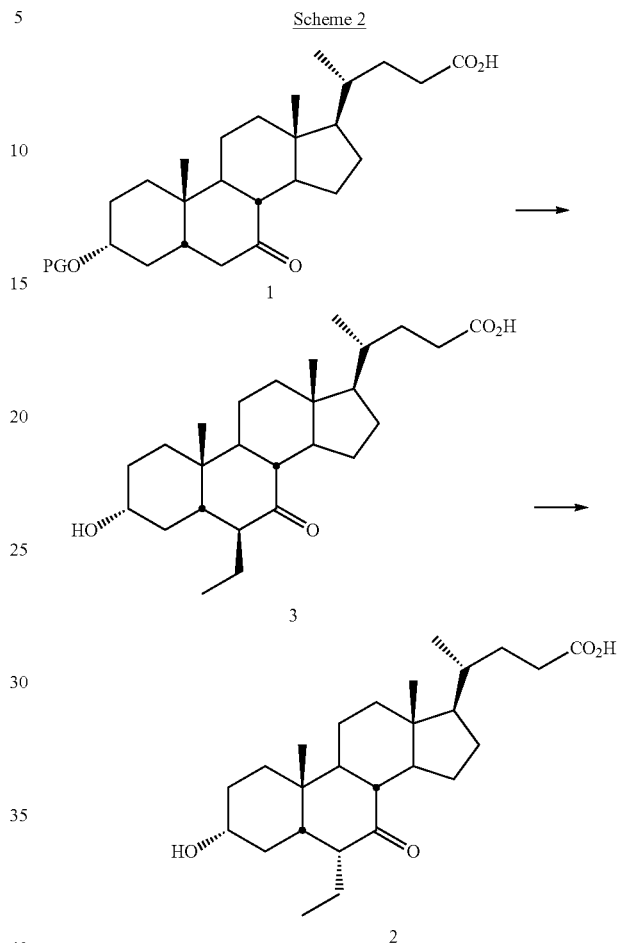

In Scheme 2, Compound 2 is prepared from Compound 1 via alkylation followed by base mediated isomerization of the 6-beta ethyl intermediate (Compound 3). Compound 1 is contacted with a base to selectively deprotonate the carbon atom at the C-6 position. Alkylation of Compound 1 with an ethyl halide, or an equivalent alkylating agent, followed by a deprotection step, produces Compound 3. Treatment of Compound 3 with a base such as a metal hydroxide produces Compound 2. In one embodiment, the metal hydroxide is sodium hydroxide. In another embodiment, the alkylation/isomerization reaction described above is carried out in two phases (starting from Compound 1). First, the alkylation is carried out and then second, the reaction mixture is heated to about 100° C. (to carry out the isomerization of the C-6 position from the beta configuration to the alpha configuration) and then cooled to 20° C. to about 40° C. The reaction mixture is heated until the isomerization is complete.

The process of the present application is an improvement over the processes disclosed previously, e.g., as in WO2002/072598 and WO2006/122977, and more recently WO2013/192097. For example, WO2013/192097 describes a process for making OCA, comprising the steps shown in Scheme A below:

Scheme A

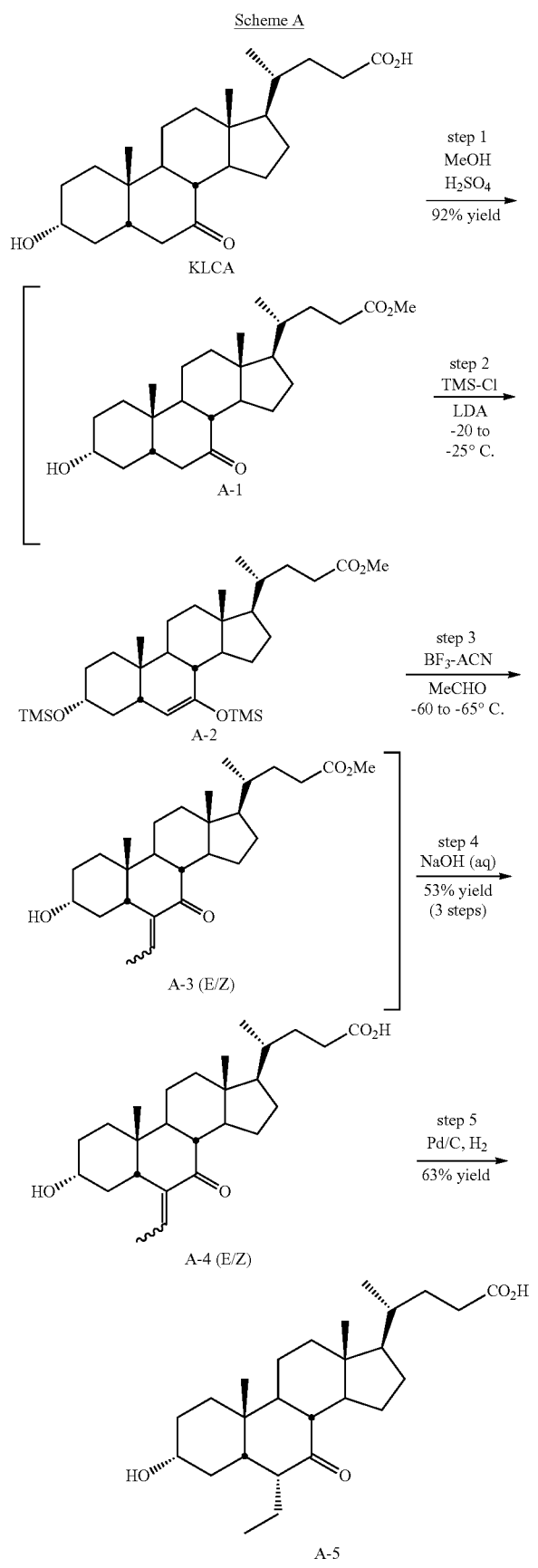

In Scheme A, Compound A-5 is prepared through a 5-step synthetic process with the starting material 7-keto lithocholic acid (KLCA). In Step 1, KLCA is esterified to form a methyl ester, Compound A-1, by heating KLCA in methanol with sulfuric acid as the catalytic reagent. Compound A-1 is isolated in 92% yield. In Step 2, Compound A-1 is treated with lithium di-isopropyl amide (LDA) in the presence of trimethylsilyl chloride (TMS-Cl) to generate Compound A-2 having both a TMS-ether at the C-3 position and a silyl enol ether at the C-7 position. In step 3, Compound A-2 is concentrated (e.g., azeotropically distilled to remove water, then concentrated to an oil), dissolved in dichloromethane (DCM), mixed with acetaldehyde, and then added to a pre-cooled (−60 to −65° C.) solution of $BF_3$-ACN complex in DCM. The mixture is warmed to 20° C. to form Compound A-3. In step 4, the solution containing Compound A-3 is concentrated, dissolved in methanol, and is subjected to hydrolysis (e.g., in NaOH aq.). The solution is acidified, extracted, and crystallized from ethyl acetate to generate Compound A-4 (53% yield, 3 steps). Optionally, Compound A-4 is recrystallized from ethanol to improve purity. However, the recrystallization results in significant yield loss. In step 5, Compound A-4 is hydrogenated to form Compound A-5, which is isolated after crystallizing from n-butyl acetate in 62% yield.

Although the process described in Scheme A offered various advantages over previous methods for preparing OCA, it may not be ideal for making OCA at a large scale due to the following:

(1) In Step 2 for preparing Compound A-2, an excess of LDA is used. LDA is not only very expensive, but it is also a strong base which may deprotonate at the C-23 position, thus leading to the formation of unintended impurities.

(2) Step 2 also needs to be carried out at the lower limit of the standard plant cooling condition, and accordingly may require specialized cryogenics.

(3) Moreover, in order to remove water from Compound A-2, azeotropic distillation is used, which not only requires an excessive amount of THF, adding to the process time and manufacturing cost, but also is not ideal in a large scale manufacturing setting.

(4) DCM used in Step 3 is not an ideal solvent for large scale manufacturing due to regulatory/environmental concerns.

(5) Further, addition of Compound A-2 in Step 3, despite being exothermic, must be completed as quickly as possible to prevent decomposition of Compound A-2 to Compound A-1.

(6) In addition, the $BF_3$-acetonitrile complex is known to crystallize at −10° C. To ensure a rapid addition of acetaldehyde to Compound A-2, an adequate amount of $BF_3$ must be available in solution. However, $BF_3$-acetonitrile tends to crystalize over time and has poor solubility. Accordingly, milling or crushing the $BF_3$-acetonitrile crystals is necessary, adding to process time and manufacturing cost.

The method of the present application provides a number of improvements compared to previously described processes. In one embodiment, having fewer number of steps, the method of the present application provides an increased yield. In one embodiment, the method of the present application produces OCA, or a pharmaceutically acceptable salt, solvate, or amino acid conjugate thereof, at least 50%, at least 55%, at least 60%, at least 65%, at least 70%, at least 75%, at least 80%, at least 85%, at least 90%, or at least 95% yield. In one embodiment, the method of the present application produces OCA at least 65%, at least 70%, at least 75%, at least 80%, at least 85%, at least 90%, or at least 95% yield.

In one embodiment, the method of the present application produces substantially pure obeticholic acid, or a pharmaceutically acceptable salt, solvate, or amino acid conjugate thereof. The term "purity" as used herein refers to the amount of obeticholic acid based on analytic methods commonly used in the art (e.g., HPLC). Purity is based on the "organic" purity of the compound, and does not include a measure of any amount of water, solvent, metal, inorganic salt, etc. In one embodiment, the purity of obeticholic acid is compared to the purity of the reference standard by comparing the area under the peak in HPLC. In one embodiment, the known standard for purity is an obeticholic acid reference standard. In one embodiment, obeticholic acid has a purity of greater than about 96%. In one embodiment, obeticholic acid has a purity of greater than about 98%. For example, the purity of obeticholic acid is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of obeticholic acid is 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of obeticholic acid is 98.0%, 98.5%, 99.0%, 99.5%, 99.6%, 99.7%, 99.8%, or 99.9%. For example, the purity of obeticholic acid is 98.5%, 99.0%, or 99.5%. In one embodiment, the purity is determined by HPLC.

In another embodiment, the purity of the obeticholic acid prepared by the method of the present application has a purity of 100% minus the amounts of water, sulphated ash, residual solvents, and other impurity contents such as 6-ethylursodeoxycholic acid, 3α-hydroxy-6α-ethyl-7-cheto-5β-cholan-24-oic acid, 6β-ethylchenodeoxycholic acid, 3α,7α-dihydroxy-6-ethyliden-5β-cholan-24-oic acid, chenodeoxycholic acid, and 3α(3α,7α-dihydroxy-6α-ethyl-5β-cholan-24-oyloxy)-7α-hydroxy-6α-ethyl-5β-cholan-24-oic acid.

In one embodiment, the obeticholic acid prepared according to the method of the present application contains less than about 10% of water, less than about 9% of water, less than 8% of water, less than 7% of water, less than 6% of water, less than 5% of water, less than 4% of water, less than 3% of water, less than 2% of water, or less than 1% of water.

In one embodiment, the obeticholic acid prepared according to the method of the present application contains not more than 0.15% of 6-ethylursodeoxycholic acid and 3α,7α-dihydroxy-6-ethyliden-5β-cholan-24-oic acid. In one embodiment, the obeticholic acid prepared according to the method of the present application contains less than about 0.07%, less than about 0.06%, or less than about 0.05% of 6-ethylursodeoxycholic acid and 3α,7α-dihydroxy-6-ethyliden-5β-cholan-24-oic acid.

In one embodiment, the obeticholic acid prepared according to the method of the present application contains not more than (NMT) 0.15% of 3α-hydroxy-6α-ethyl-7-cheto-5β-cholan-24-oic acid. In one embodiment, the obeticholic acid prepared according to the method of the present application contains less than about 0.07%, less than about 0.06%, or less than about 0.05% of 3α-hydroxy-6α-ethyl-7-cheto-5β-cholan-24-oic acid.

In one embodiment, the obeticholic acid prepared according to the method of the present application contains not more than (NMT) 0.15% of 6β-ethylchenodeoxycholic acid. In one embodiment, the obeticholic acid prepared according to the method of the present application contains less than about 0.07%, less than about 0.06%, or less than about 0.05% of 6β-ethylchenodeoxycholic acid.

In one embodiment, the obeticholic acid prepared according to the method of the present application contains no more than (NMT) 3% of chenodeoxycholic acid (CDC). In one embodiment, the obeticholic acid prepared according to the method of the present application contains less than about 1%, less than about 0.3%, or less than about 0.2% of CDCA.

In one embodiment, the obeticholic acid prepared according to the method of the present application contains no more than (NMT) 4% of CDCA and 6-ethylursodeoxycholic acid.

In one embodiment, the obeticholic acid prepared according to the method of the present application contains no more than (NMT) 1.5% of 3α(3α,7α-dihydroxy-6α-ethyl-5β-cholan-24-oyloxy)-7α-hydroxy-6α-ethyl-5β-cholan-24-oic acid. In one embodiment, the obeticholic acid prepared according to the method of the present application contains less than about 1%, less than about 0.07%, less than about 0.06%, or less than about 0.05% of 3α(3α,7α-dihydroxy-6α-ethyl-5β-cholan-24-oyloxy)-7α-hydroxy-6α-ethyl-5β-cholan-24-oic acid.

The present application provides methods for the synthesis of highly pure obeticholic acid which is safe and which produce obeticholic acid on a large scale. In one embodiment, obeticholic acid is produced on a commercial scale process. In one embodiment, the method of the present application produces obeticholic acid in high yield (>80%) and with limited impurities.

The present application also relates to a method of preparing 6α-ethyl-3α,7α-23-trihydroxy-24-nor-5β-cholan-23-sulfate (Compound 9):

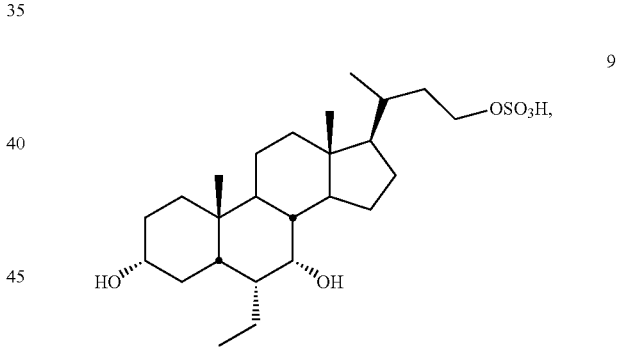

9 or a pharmaceutical acceptable salt, solvate, or amino acid conjugate thereof, comprising:

a) esterifying OCA to form Compound 4:

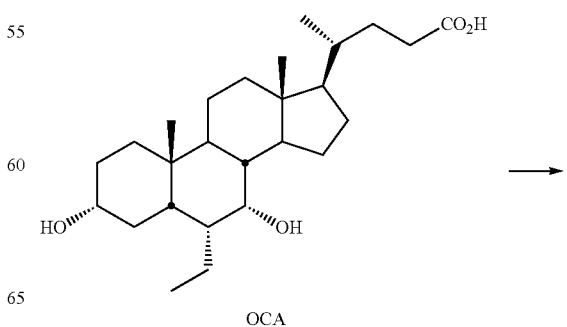

OCA

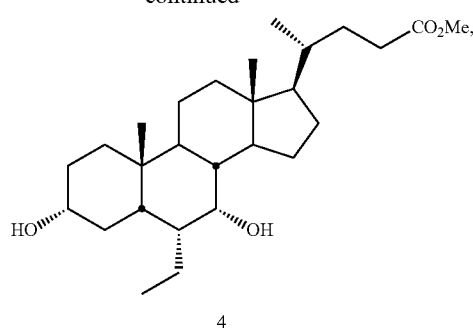
4
b) converting Compound 4 to form Compound 5:
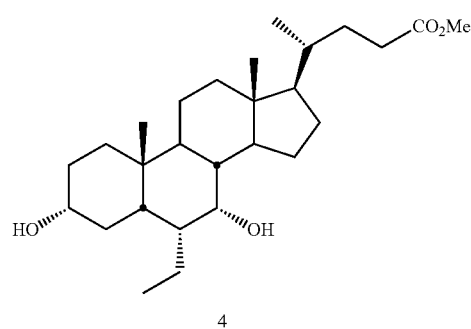
4
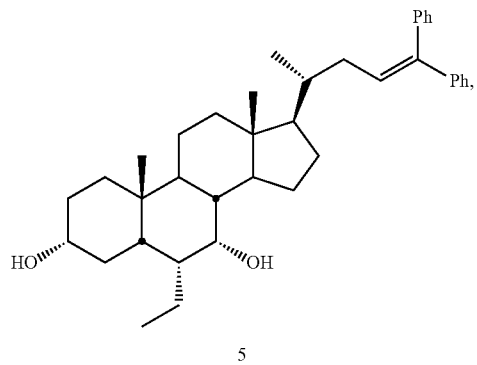
5
c) converting Compound 5 to form Compound 6:
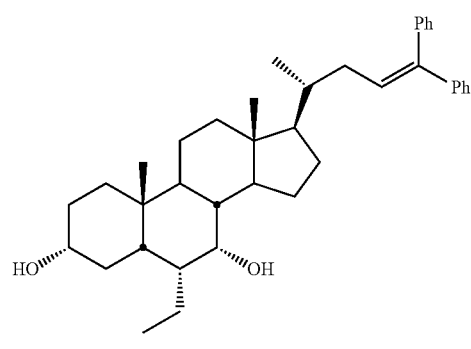
5
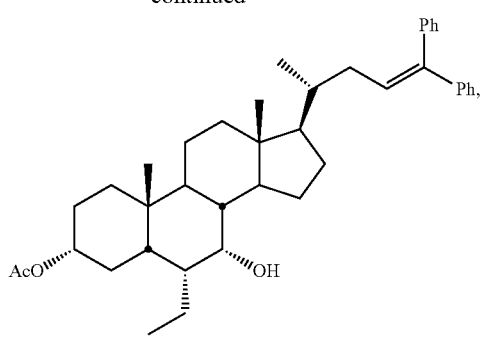
6
d) converting Compound 6 to form Compound 7:
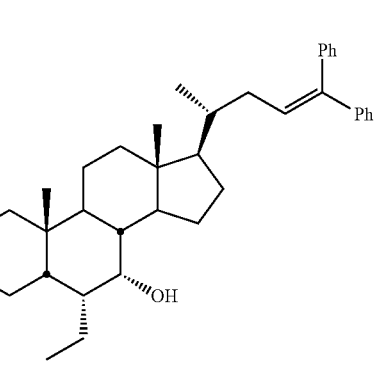
6
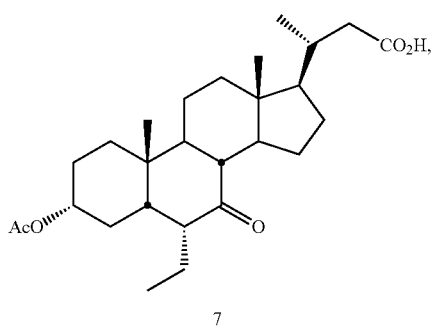
7
e) converting Compound 7 to form Compound 8:
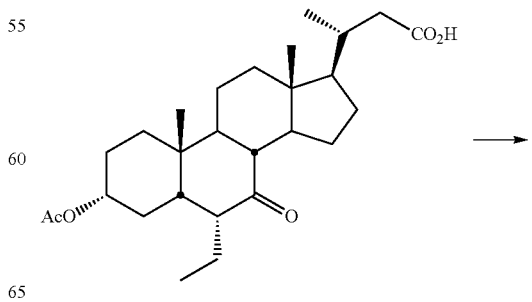
7

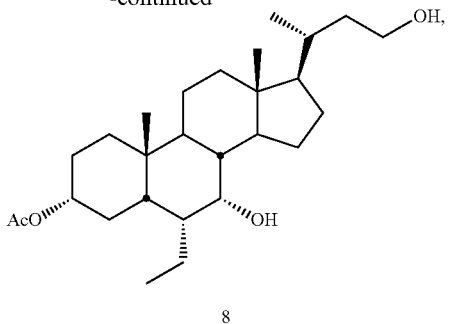

8 and
f) converting Compound 8 to form Compound 9:

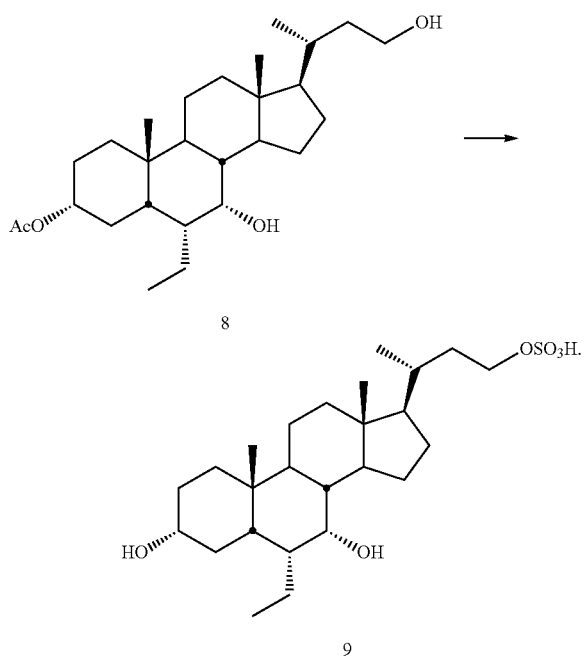

In one embodiment, the method further comprises preparing the sodium salt of Compound 9:

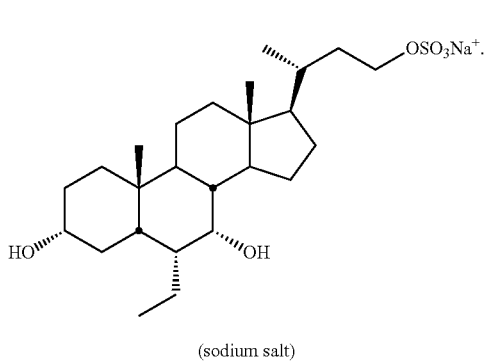

(sodium salt)

Step a) involves the esterification of OCA to form Compound 4. In one embodiment, the reaction is conducted in methanol. In another embodiment, the reaction is catalyzed with an acid. In one embodiment, the acid is p-toulenesulfonic acid. In one embodiment, the acid is sulfuric acid or methanesulfonic acid. In one embodiment, the esterification is performed at a temperature from about 55° C. to about 85° C., e.g., 55° C. 65° C., 75° C., and 85° C., as well as any temperature increment in between.

Step b) involves a Grignard reaction to afford Compound 5 via the formation of a diphenyl carbinol intermediate. In one embodiment, Compound 4 is first contacted with phenylmagnesium bromide to afford the diphenyl carbinol intermediate. In another embodiment, the molar ratio of phenylmagnesium bromide to Compound 4 is about 6:1. In another embodiment, the molar ratio of phenylmagnesium bromide to Compound 4 is about 5:1. In one embodiment, the reaction is performed in a non-erotic solvent. In one embodiment, the non-protic is tetrahydrofuran. In one embodiment, an acid is added to the reaction after the formation of the diphenyl carbinol intermediate. In one embodiment, the acid is p-toluenesulfonic acid. In one embodiment, the reaction is performed at a temperature from about 50° C. to about 90° C., e.g., 50° C., 60° C., 70° C., 75° C., 80° C., and 90° C., as well as any temperature increment in between.

Step c) involves the protection of the hydroxyl group at the C-3 position of Compound 5 to afford Compound 6. In one embodiment, Compound 5 is contacted with acetic anhydride. In one embodiment, the molar ratio of acetic anhydride to Compound 5 is about 2:1. In another embodiment, the molar ratio is about 1.66. In one embodiment, the reaction is catalyzed by 4-dimethylaminopyridine (DMAP). In another embodiment, pyridine is added to the reaction. In another embodiment, the reaction is performed in diethyl ether or tetrahydrofuran. In one embodiment, the reaction is performed at a temperature below 30° C.

Step d) involves the oxidative cleavage of the double bond and the oxidation of the hydroxyl group at the C-7 position of Compound 6 to afford Compound 7. In one embodiment, Compound 6 is contacted with $RuCl_3$, $NaIO_4$, and an acid. In one embodiment, the molar ratio of Compound 6 to $RuCl_3$ is from about 18:1 to about 22:1. In one embodiment, the molar ratio of Compound 6 to $RuCl_3$ is from about 19:1 to about 21:1. In another embodiment, the molar ratio of Compound 6 to $RuCl_3$ is about 20:1. In one embodiment, the acid is selected from $H_2SO_4$, HCl, $HClO_4$, and $HIO_4$. In one embodiment, the acid is 2N $H_2SO_4$. In another embodiment, the acid is 2N HCl. In one embodiment, the molar ratio of Compound 6 to the acid is from about 2:1 to about 6:1. In one embodiment, the molar ratio of Compound 6 to the acid is from about 3:1 to about 5:1. In another embodiment, the molar of Compound 6 to the acid ratio is about 4:1. In one embodiment, the reaction is carried out at a temperature from about −10° C. to about 10° C. In another embodiment, the temperature is from about −5° C. to about 5° C. In another embodiment, the temperature is about 0° C. In one embodiment, the reaction is carried out in a mixture of solvents. In one embodiment, the mixture of solvents comprises one polar protic and two polar aprotic solvents. In one embodiment, the polar protic solvent is $H_2O$. In one embodiment, the polar aprotic solvents are acetonitrile and ethyl acetate. In one embodiment, the polar aprotic solvents are acetonitrile and chloroform. In one embodiment, the mixture of solvents is $H_2O$/ethyl acetate/acetonitrile. In one embodiment, the ratio of $H_2O$ to ethyl acetate to acetonitrile is from about 1:1:1 to about 1:3:2 by volume. In another embodiment, the ratio is about 1:1.5:1 to about 1:2.5:1.5 by volume. In another embodiment, the ratio is about 1:2:1.5 by volume.

Step e) involves the reduction of the C-23 carboxylic acid and C-7 carbonyl group of Compound 7 to afford Compound 8. In one embodiment, Compound 7 is contacted with a chloroformate, a base, and a reducing agent. In one embodiment, the chloroformate is isobutyl chloroformate, ethyl chloroformate, isopropyl chloroformate, or t-butyl chloroformate. In one embodiment, the chloroformate is isobutyl chloroformate. In one embodiment, the base is triethylamine. In one embodiment, the reducing agent is sodium borohydride or sodium triacetoxyborohydride. In one embodiment, the reaction is carried out in a polar aprotic solvent. In one embodiment, the polar aprotic solvent is tetrahydrofuran. In one embodiment, the reaction is carried out at a temperature from about −10° C. to about 10° C. In embodiment, the temperature is from about −5° C. to about 5° C. In another embodiment, the temperature is about 0° C.

Step f) involves the sulfation of the hydroxyl group at the C-23 position and deprotection of the hydroxyl group at the C-3 position of Compound 8 to afford Compound 9. In one embodiment, the sulfation is conducted with sulfur trioxide, chlorosulfonic acid, or sulphamic acid. In one embodiment, the sulfation is conducted with a sulfur trioxide complex. In one embodiment, the sulfur trioxide complex is selected from sulfur trioxide pyridine, sulfur trioxide dioxane, and sulfur trioxide trimethylamine. In one embodiment, the sulfur trioxide complex is sulfur trioxide pyridine.

In one embodiment, and the reaction mixture is treated with a base and a polar protic solvent to form the sodium salt of Compound 9. In one embodiment, the polar protic solvent is $CH_3OH$. In one embodiment, the base is NaOH. In one embodiment, the base is 10% (w/w) solution of NaOH in $CH_3OH$.

The present application further relates to a method of preparing a compound of Formula III as described in Scheme 3.

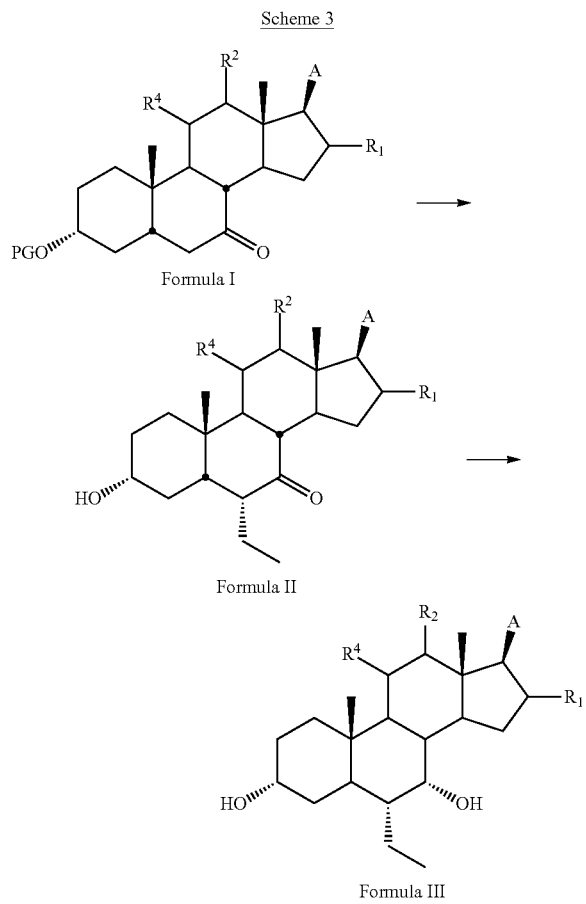

wherein:
A is

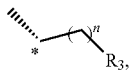

oxadiazolonyl, or isoxazolonyl, wherein the carbon atom marked with "*" is bonded to the carbon atom to which A is bonded;

n is 0, 1, or 2;

$R^1$, $R^2$, and $R^4$ are each independently H or OH;

$R^3$ is $(CR^5R^6)_pC(O)OH$, $(CR^5R^6)_pOH$, $(CR^5R^6)_pOSO_3H$; $(CR^5R^6)_pSO_3H$; $C(O)NHR^7$, tetrazolyl, oxadiazolyl, oxadiazolonyl, or thiazolidine-dionyl optionally substituted with $NHS(O)_2$—$(C_1-C_3)$ alkyl;

$R^5$ and $R^6$ are each independently H, halogen, OH, or alkyl optionally substituted with OH or halogen, $R^7$ is OH, $(CH_2)_pOH$, or $(CH_2)_pOSO_3H$;

p is 1 or 2; and

PG is a protecting group.

In general, a compound of Formula I is treated with an alkylating agent to form a compound of Formula II which is further converted to the compound of Formula III by methods known in the art. In one embodiment, the alkylating agent is selected from alkyl halide (e.g., ethyl halide), alkyl tosylate (e.g., ethyl tosylate), alkyl mesylate (e.g., ethyl mesylate), sulfonate ester (e.g., sulfonate ethyl ester), alkyl oxonium salt (e.g., $Et_3O.BF_4$), dialkyl sulfate (e.g., diethyl sulfate), dialkyl carbonate (e.g., diethyl carbonate), and tetraalkylammonium salt (e.g., tetraethylammonium salt). In one embodiment, the alkylating agent is alkyl halide. In one embodiment, the alkylating agent is ethyl halide (Et-X), wherein Et is ethyl and X is halogen (e.g., F, Cl, Br, or I). In one embodiment, the alkyl halide is ethyl bromide or ethyl iodide. In one embodiment, the alkyl halide is ethyl bromide. In one embodiment, the alkylation is conducted in an aprotic solvent. In one embodiment, the aprotic solvent is selected from tetrahydrofuran (THF), ethyl acetate (EtOAc), acetone, dimethylformamide (DMF), acetonitrile (MeCN), dimethyl sulfoxide (DMSO), toluene, hexane, benzene, 1,4-dioxane, chloroform, dichloromethane (DCM), diethyl ether, and methyl tert-butyl ether (MTBE). In one embodiment, the aprotic solvent is selected from THF, MTBE, toluene, and DMF.

In one embodiment, the alkylation is conducted in the presence of a deprotonating agent. In one embodiment, the deprotonating agent is selected from $C_1-C_6$ alkoxide (e.g., methoxide, ethoxide, propoxide, iso-propoxide, butoxide, iso-butoxide, tert-butoxide, pentoxide, iso-pentoxide, test-pentoxide, and hexyloxide), metal hydroxide, and metal hydride. In one embodiment, the deprotonating agent is metal $C_1-C_6$ alkoxide, such as sodium tert-butoxide, potassium test-butoxide, sodium test-pentoxide, and potassium tert-pentoxide. In one embodiment, the deprotonating agent is a metal hydroxide, such as sodium hydroxide and potassium hydroxide. In one embodiment, the deprotonating agent is a metal hydride, such as sodium hydride and potassium hydride. One skilled in the art will recognize which metal hydride functions as a deprotonating agent instead of a reducing agent.

In one embodiment, the compound of Formula III is selected from the group consisting of

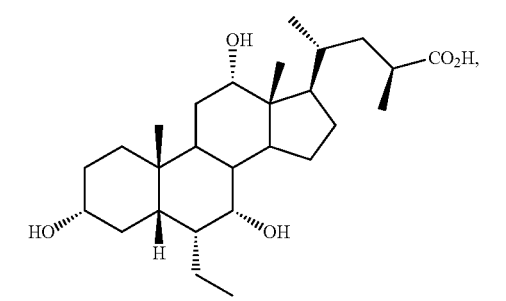
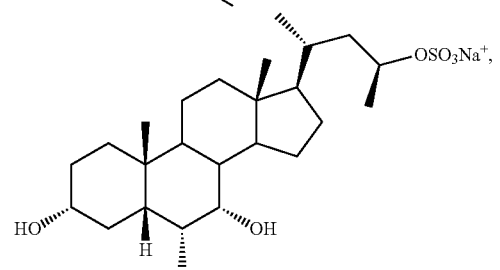
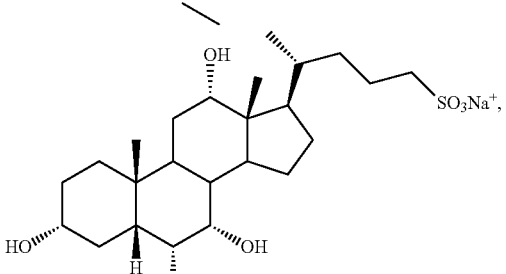
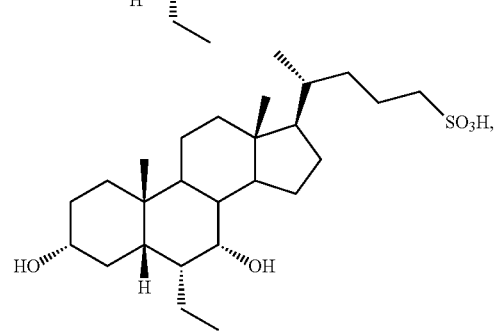
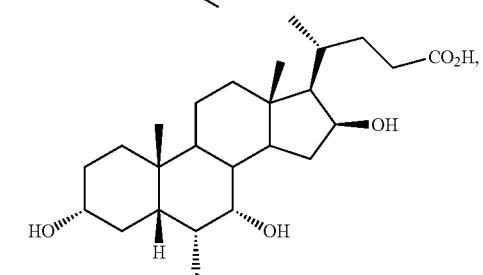
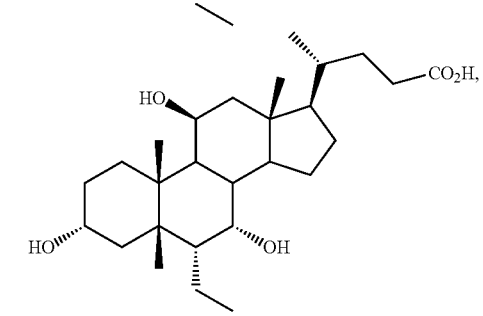
-continued
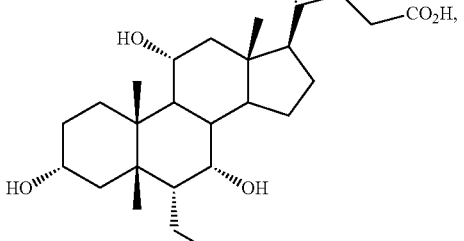
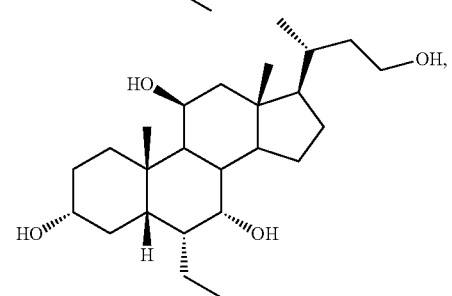
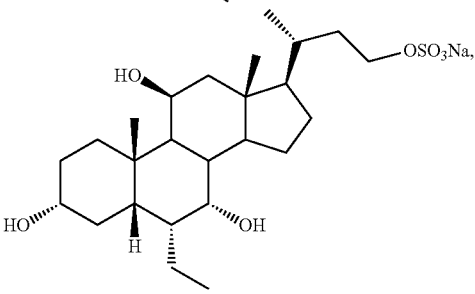
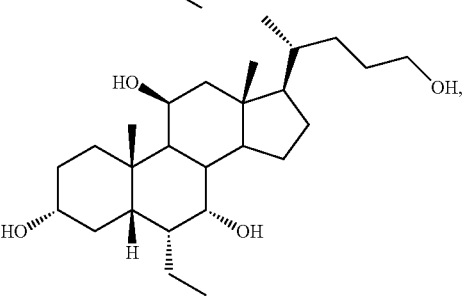
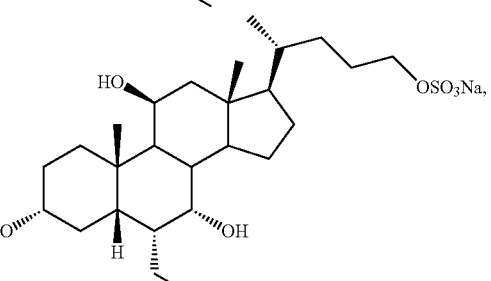
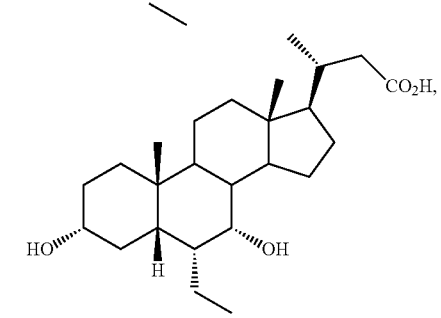

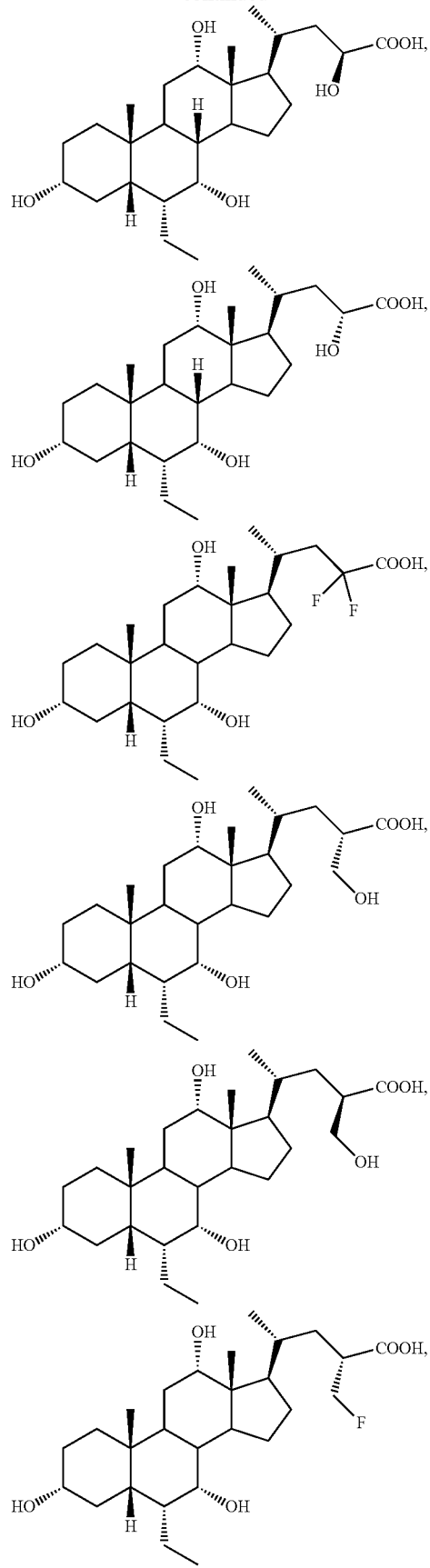

31
-continued

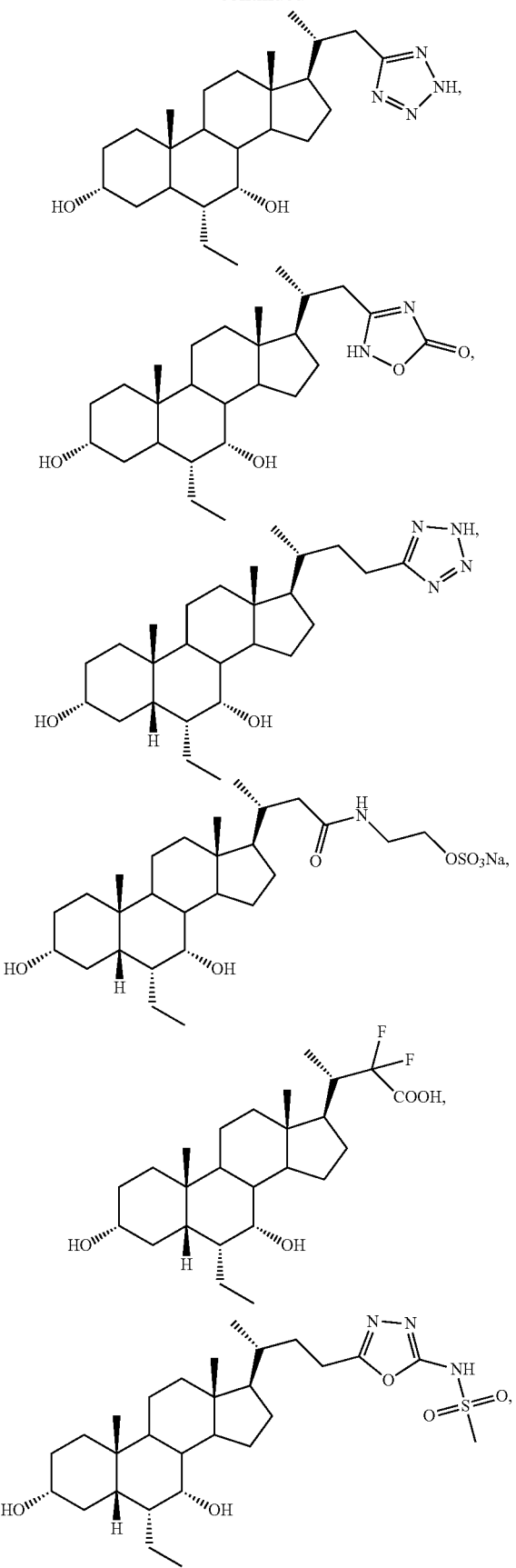

32
-continued

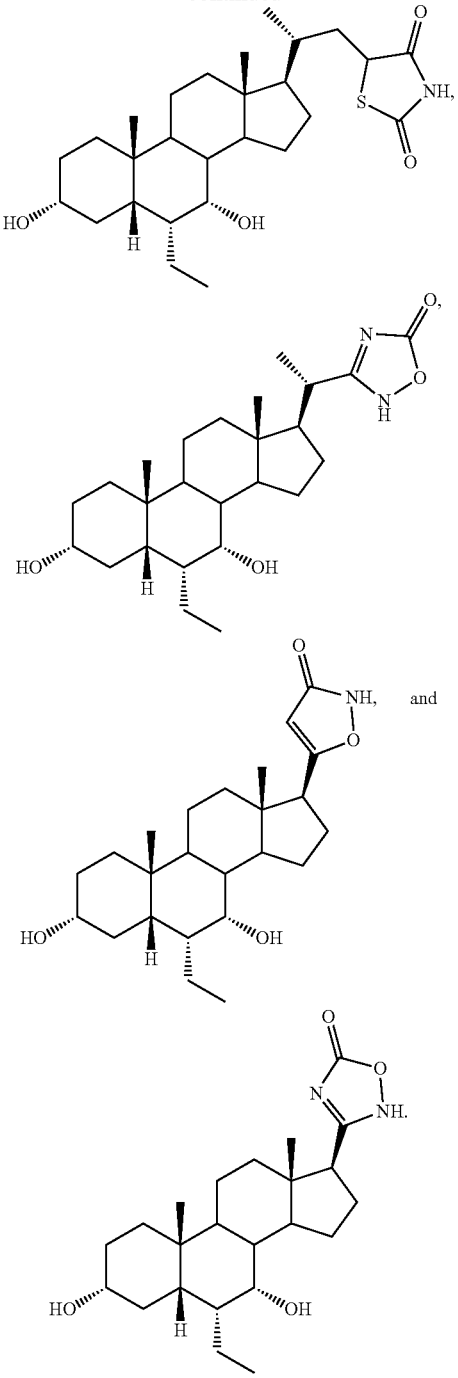 [SMILES: CC[C@H]1[C@@H](O)C2C3CC[C@H]([C@H](C)CC4SC(=O)NC4=O)[C@@]3(C)CCC2[C@@]2(C)CC[C@@H](O)C[C@@H]12 ; CC[C@H]1[C@@H](O)C2C3CC[C@H]([C@H](C)c4nc(=O)o[nH]4)[C@@]3(C)CCC2[C@@]2(C)CC[C@@H](O)C[C@@H]12 ; CC[C@H]1[C@@H](O)C2C3CC[C@H](c4cc(=O)[nH]o4)[C@@]3(C)CCC2[C@@]2(C)CC[C@@H](O)C[C@@H]12 ; CC[C@H]1[C@@H](O)C2C3CC[C@H](c4nc(=O)o[nH]4)[C@@]3(C)CCC2[C@@]2(C)CC[C@@H](O)C[C@@H]12]

Oral Formulation and Administration

The present application provides a compound of the invention for oral administration. In one embodiment, the formulation relates to an oral administration for the prevention and treatment of FXR mediated diseases and conditions.

Formulations suitable for oral administration may be provided as discrete units, such as tablets, capsules, cachets (wafer capsule used by pharmacists for presenting a drug), lozenges, each containing a predetermined amount of a compound of the invention; as powders or granules; as solutions or suspensions in aqueous or non-aqueous liquids; or as oil-in-water or water-in-oil emulsions.

Formulations of the present application may be prepared by any suitable method, typically by uniformly and intimately admixing a compound of the invention with liquids or finely divided solid carriers or both, in the required proportions and then, if necessary, shaping the resulting mixture into the desired shape.

For example, a tablet may be prepared by compressing an intimate mixture comprising a powder or granules of a compound of the invention and one or more optional ingredients, such as a binder, lubricant, inert diluent, or surface active dispersing agent, or by molding an intimate mixture of powdered active ingredient and inert liquid diluent.

For example, one or more tablets may be administered to get to a target dose level based on the subject's weight, e.g., a human between about 30 kg to about 70 kg.

In addition to the ingredients specifically mentioned above, the oral formulations of the present application may include other agents known to those skilled in the art of pharmacy, having regard for the type of formulation in issue. Oral formulations may include suitable flavoring agents.

In one embodiment, the present application relates to a pharmaceutical formulation of a compound of the invention, or a pharmaceutically acceptable salt, solvate, or amino acid conjugate thereof, wherein the compound of the invention is produced by a process of the application. In another embodiment, the formulation is administered orally.

In one embodiment, the formulation is in tablet form. In another embodiment, the formulation comprises a compound of the invention and one or more components selected from microcrystalline cellulose, sodium starch glycolate, magnesium stearate, coating material, and colloidal silicon dioxide. In one embodiment, the coating material is an Opadry® coating material.

All percentages and ratios used herein, unless otherwise indicated, are by weight or molar equivalents. The percent dimeric impurity is calculated on an area percent basis, typically as quantified by analytical HPLC.

Pharmaceutical Compositions

A compound of the invention is useful for a variety of medicinal purposes. A compound of the invention may be used in methods for the prevention or treatment of FXR mediated diseases and conditions. In one embodiment, the disease or condition is selected from biliary atresia, cholestatic liver disease, chronic liver disease, nonalcoholic steatohepatitis (NASH), hepatitis C infection, alcoholic liver disease, primary biliary cirrhosis (PBC), liver damage due to progressive fibrosis, liver fibrosis, and cardiovascular diseases including atherosclerosis, arteriosclerosis, hypercholesteremia, and hyperlipidemia. In one embodiment, a compound of the invention may be used in methods for lowering triglycerides and/or increasing HDL. Other effects of a compound of the invention include lowering alkaline phosphatase (ALP), bilirubin, ALT, AST, and/or GGT. In one embodiment, the present application relates to a pharmaceutical composition comprising a compound of the invention and a pharmaceutically acceptable carrier, wherein the compound of the invention is produced by a method of the present application.

In one embodiment, the compound or pharmaceutical composition is administered orally, parenterally, or topically. In one embodiment, the compound or pharmaceutical composition is administered orally.

In one embodiment, the present application relates to a method for inhibiting fibrosis in a subject who is suffering from a cholestatic condition, the method comprising the step of administering to the subject an effective amount of a compound of the invention, wherein the compound of the invention is produced by the method of the present application. In one embodiment, the present application relates to a method for inhibiting fibrosis in a subject who is not suffering from a cholestatic condition, the method comprising the step of administering to the subject an effective amount of a compound of the invention, wherein the compound of the invention is produced by the method of the present application. In one embodiment, the fibrosis to be inhibited occurs in an organ where FXR is expressed.

In one embodiment, the cholestatic condition is defined as having abnormally elevated serum levels of alkaline phosphatase, 7-glutamyl transpeptidase (GGT), and 5' nucleotidase. In another embodiment, the cholestatic condition is further defined as presenting with at least one clinical symptom. In another embodiment, the symptom is itching (pruritus). In another embodiment, the fibrosis is selected from the group consisting of liver fibrosis, kidney fibrosis, and intestinal fibrosis. In another embodiment, the cholestatic condition is selected from the group consisting of primary biliary cirrhosis, primary sclerosing cholangitis, drug-induced cholestasis, hereditary cholestasis, and intrahepatic cholestasis of pregnancy. In another embodiment, the subject is not suffering from a cholestatic condition associated with a disease or condition selected from the group consisting of primary liver and biliary cancer, metastatic cancer, sepsis, chronic total parenteral nutrition, cystic fibrosis, and granulomatous liver disease.

In one embodiment, the subject has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; ai-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In one embodiment, the subject has intestinal fibrosis associated with a disease selected from the group consisting of Crohn's disease, ulcerative colitis, post-radiation colitis, and microscopic colitis.

In one embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

Definitions

As used herein, a "compound of the invention" refers to obeticholic acid (OCA), 6α-ethyl-3α, 7α-23-trihydroxy-24-nor-5β-cholan-23-sulfate (Compound 9), or a pharmaceutically acceptable salt, solvate, or amino acid conjugate thereof.

As used herein, "alkyl" refers to saturated and unsaturated aliphatic groups. Saturated aliphatic groups include, but are not limited to, straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_1$-$C_6$ for straight chain, $C_3$-$C_6$ for branched chain). In some examples, a straight chain, or branched chain alkyl has four or fewer carbon atoms in its backbone. Further, cycloalkyls can have from three to eight carbon atoms in their ring structure. Unsaturated aliphatic groups include alkenyl groups (e.g., ethenyl, 1-propenyl, 2-propenyl, 1-butenyl, 2-butenyl and 3-butenyl) and alkynyl groups (e.g. ethynyl, 1-propynyl, 2-propynyl, 1-butynyl, 2-butynyl, 3-butynyl and 5-but-1-en-3-ynyl) to ethyl, propyl and allyl.

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms; or relieving the disease state, i.e., causing temporary or permanent regression of the disease state or its clinical symptoms.

"Preventing" the disease state includes causing the clinical symptoms of the disease state not to develop in a subject that may be exposed to or predisposed to the disease state, but does not yet experience or display symptoms of the disease state.

"Disease state" means any disease, disorder, condition, symptom, or indication.

As used herein, the term "about" or "approximately", or the like, when used together with a numeric value, may include a range of numeric values which is more or less than the numeric value to which the term refers or relate. For example, the range can include numeric values that are from 10% less to 10% more, from 9% less to 9% more, from 8% less to 8% more, from 7% less to 7% more, from 6% less to 6% more, from 5% less to 5% more, from 4% less to 4% more, from 3% less to 3% more, from 2% less to 2% more, or from 1% less to 1% more, than the numeric value to which the term refers or relate. For example, "about 5" can include numeric values from 4.5 to 5.5, from 4.55 to 5.45, from 4.6 to 5.4, from 4.65 to 5.35, from 4.7 to 5.3, from 4.75 to 5.25, from 4.8 to 5.2, from 4.85 to 5.15, from 4.9 to 5.1, or from 4.95 to 5.05.

The term "effective amount", as used herein, refers to an amount of a compound of the invention (e.g., an FXR-activating ligand) that produces an acute or chronic therapeutic effect upon appropriate dose administration. The effect includes the prevention, correction, inhibition, or reversal of the symptoms, signs and underlying pathology of a disease/condition (e.g., fibrosis of the liver, kidney, or intestine) and related complications to any detectable extent.

"A therapeutically effective amount" means the amount of a compound of the invention that, when administered to a mammal for treating a disease, is sufficient to effect such treatment for the disease. The "therapeutically effective amount" will vary depending on the disease and its severity and the age, weight, etc., of the mammal to be treated.

A therapeutically effective amount of a compound of the invention can be formulated with a pharmaceutically acceptable carrier for administration to a human or an animal. Accordingly, a compound of the invention or its formulations can be administered, for example, via oral, parenteral, or topical routes, to provide an effective amount of the compound. In alternative embodiments, a compound of the invention prepared in accordance with the present application can be used to coat or impregnate a medical device, e.g., a stent.

The application also comprehends isotopically-labeled compounds of the invention, or pharmaceutically acceptable salts, solvate, or amino acid conjugates thereof, which are identical to those recited in the application and following, but for the fact that one or more atoms are replaced by an atom having an atomic mass or mass number different from the atomic mass or mass number most commonly found in nature. Examples of isotopes that can be incorporated into a compound of the invention include isotopes of hydrogen, carbon, nitrogen, fluorine, such as $^3H$, $^{11}C$, $^{14}C$ and $^{18}F$.

Tritiated. i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples of the application, by substituting a readily available isotopically labeled reagent for a non-isotopically labeled reagent. In one embodiment, a compound of the invention is not isotopically labelled. In one embodiment, a deuterated compound of the invention is useful for bioanalytical assays. In another embodiment, a compound of the invention is radiolabelled.

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Solvates" means solvent addition forms that contain either stoichiometric or non stoichiometric amounts of solvent. A compound of the invention may have a tendency to trap a fixed molar ratio of solvent molecules in the crystalline solid state, thus forming a solvate. If the solvent is water, the solvate formed is a hydrate. When the solvent is alcohol, the solvate formed is an alcoholate. Hydrates are formed by the combination of one or more molecules of water with one of the substances in which the water retains its molecular state as $H_2O$, such combination being able to form one or more hydrate, Additionally, compounds of the present application, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Tautomers" refers to compounds whose structures differ markedly in the arrangement of atoms, but which exist in rapid equilibrium. It is to be understood that a compound of the invention may be depicted as different tautomers. It should also be understood that when a compound of the invention and synthetic intermediates of the application have tautomeric forms, all tautomeric forms are intended to be within the scope of the application, and the naming of a compound of the invention does not exclude any tautomer form. A compound of the invention and synthetic intermediates of the application can exist in several tautomeric forms, including the keto-enol. For example, in keto-enol tautomerism a simultaneous shift of electrons and a hydrogen atom occurs. Tautomers exist as mixtures of a tautomeric set in solution. In solid form, usually one tautomer predominates. Even though one tautomer may be described, the present application includes all tautomers of the present compounds.

A "pharmaceutical composition" is a formulation containing a compound of the invention in a form suitable for administration to a subject. In one embodiment, the pharmaceutical composition is in bulk or in unit dosage form. It can be advantageous to formulate compositions in dosage unit form for ease of administration and uniformity of dosage. Dosage unit form, as used herein, refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the application are dictated by and directly dependent on the unique characteristics of the active reagent and the particular therapeutic effect to be achieved, and the limitations inherent in the art of compounding such an active agent for the treatment of individuals.

The unit dosage form is any of a variety of forms, including, for example, a capsule, an IV bag, a tablet, a single pump on an aerosol inhaler, or a vial. The quantity of a compound of the invention (e.g., a formulation of a compound of the invention, or a pharmaceutically acceptable salt, solvate, or amino acid conjugate thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, a compound of the invention is mixed under sterile conditions with a pharmaceutically acceptable carrier, and with any preservatives, buffers, or propellants that are required.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human. In one embodiment, the subject is a human child (e.g., between about 30 kg to about 70 kg). In one embodiment, the human child has had a Kasai procedure, where the Kasai procedure effectively gives them a functional bile duct when they are born either without a bile duct or it is completely blocked at birth.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

While it is possible to administer a compound of the invention directly without any formulation, the compound of the invention is usually administered in the form of pharmaceutical formulations comprising a pharmaceutically acceptable excipient and the compound of the invention. These formulations can be administered by a variety of routes including oral, buccal, rectal, intranasal, transdermal, subcutaneous, intravenous, intramuscular, and intranasal. Oral formulations of a compound of the invention are described further herein under the section entitled "Oral Formulation and Administration".

In one embodiment, a compound of the invention can be administered transdermally. In order to administer transdermally, a transdermal delivery device ("patch") may be needed. Such transdermal patches may be used to provide continuous or discontinuous infusion of a compound of the present application in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what is an abnormally elevated blood level for each of the markers. For example, a patient suffering from a cholestatic condition generally has greater than about 125 IU/L alkaline phosphatase, greater than about 65 IU/L GGT, and greater than about 17 NIL 5' nucleotidase in the blood. Because of the variability in the level of serum markers, a cholestatic condition may be diagnosed on the basis of abnormal levels of these three markers in addition to at least one of the symptoms mentioned above, such as itching (pruritus).

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The application having now been described by way of written description, those of skill in the art will recognize that the application can be practiced in a variety of embodiments and that the foregoing description and examples below are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art to which this application belongs. In the case of conflict, the present specification will control.

EXAMPLES

Example 1: Preparation of Compound 1a

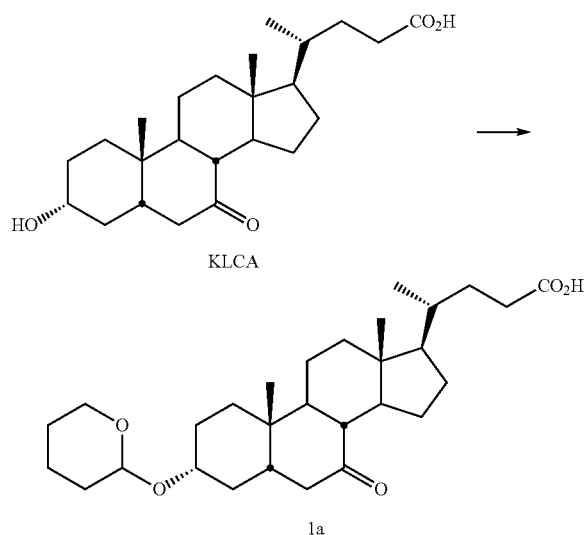

p-Toulenesulfonic acid and 3,4-dihydro-2H-pyrane are added to a solution of KLCA in dioxane. The mixture is stirred at room temperature and then treated with methanol saturated with ammonia until the solution reaches a pH of about 8-9. The solvents are removed under vacuum. The resultant residue is extracted with chloroform and washed with a saturated aqueous $NaHCO_3$ solution. After drying over $Na_2SO_4$ and removal of the solvents under vacuum, the desired product is purified by silica gel chromatography.

Example 2: Preparation of Compound 2

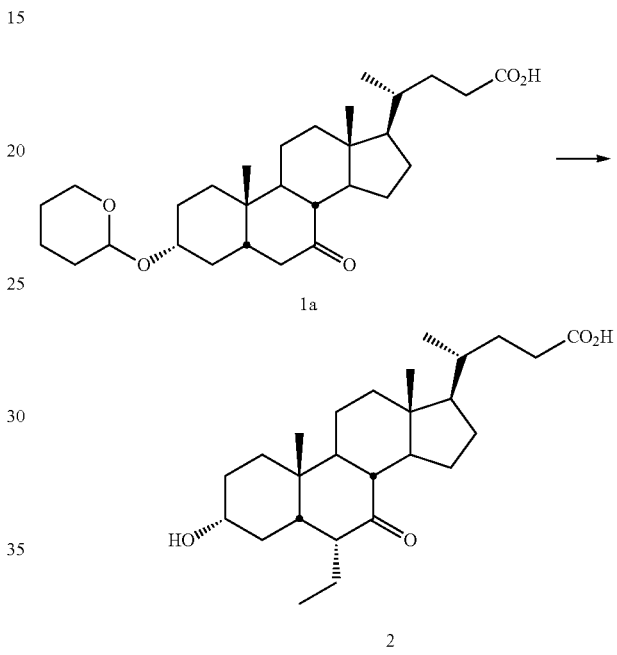

A solution of potassium tert-butoxide in anhydrous THF is cooled to about 0° C. Compound 1a dissolved in anhydrous THF is added dropwise to the solution. After 3 hr, ethyl bromide dissolved in anhydrous THE is slowly added and the mixture is allowed to warm to room temperature overnight. The solvents are removed under vacuum, acidified with 10% HCl and extracted with ethyl acetate, and washed with brine. After drying over $Na_2SO_4$ and evaporation under vacuum, the crude residue is refluxed in a solution of 2N HCl in EtOH. The residue is evaporated under vacuum and extracted with ethyl acetate, washed with a saturated $NaHCO_3$ solution, dried with $Na_2SO_4$ and evaporated under vacuum. The desired product is purified by silica gel chromatography.

Alternatively, ethyl bromide in example 2 may be replaced with an equivalent alkylating agent such as ethyl tosylate, ethyl mesylate, sulfonate ethyl ester, $Et_3O.BF_4$, diethyl sulfate, diethyl carbonate, or tetraethylammonium salt under appropriate reaction conditions. Potassium tert-butoxide in example 2 may be replaced with an equivalent deprotonating agent such as sodium tert-butoxide, sodium tert-pentoxide, and potassium tert-pentoxide under appropriate reaction conditions.

Example 3: Preparation of OCA

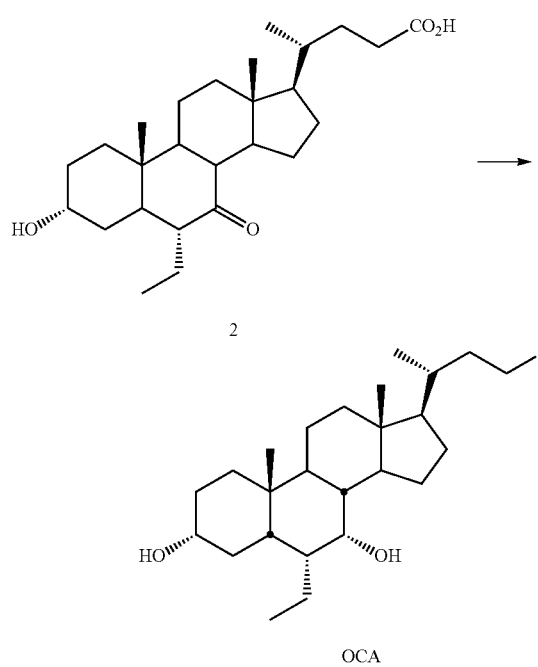

A solution of Compound 2 in aqueous NaOH is heated to 90° C. and contacted with sodium borohydride. The mixture is cooled and quenched with an aqueous citric acid solution in the presence of n-butyl acetate. The organic layer is separated and partially evaporated to induce crystallization. The suspension is filtered and the solids are washed with n-butyl acetate to afford OCA.

Example 4: Preparation of Compound 4

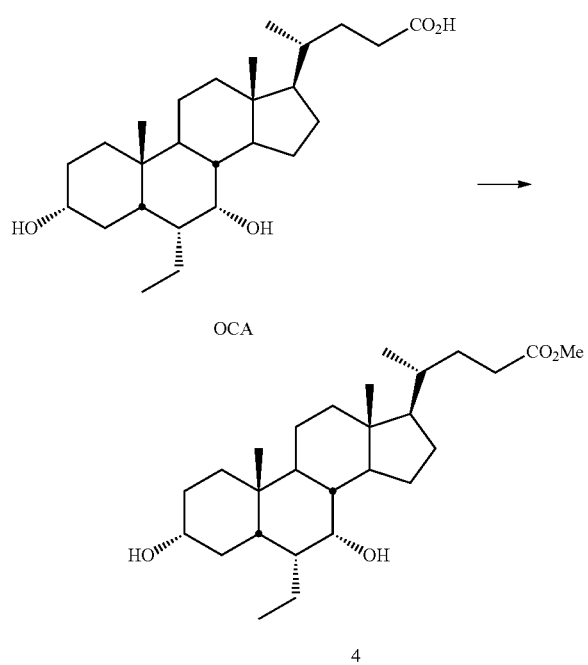

p-Toluenesulfonic acid monohydrate is added to a stirring solution of OCA in methanol and the reaction mixture is sonicated until complete disappearance of OCA, which takes approximately 3 hr. The solvent is evaporated under vacuum and the resulting residue is dissolved in methylene chloride, and washed with a saturated aqueous solution of sodium bicarbonate, water, and brine. The combined organic layers are dried over anhydrous sodium sulfate, and the solvent is evaporated under vacuum to afford Compound 4.

Example 5: Preparation of Compound 5

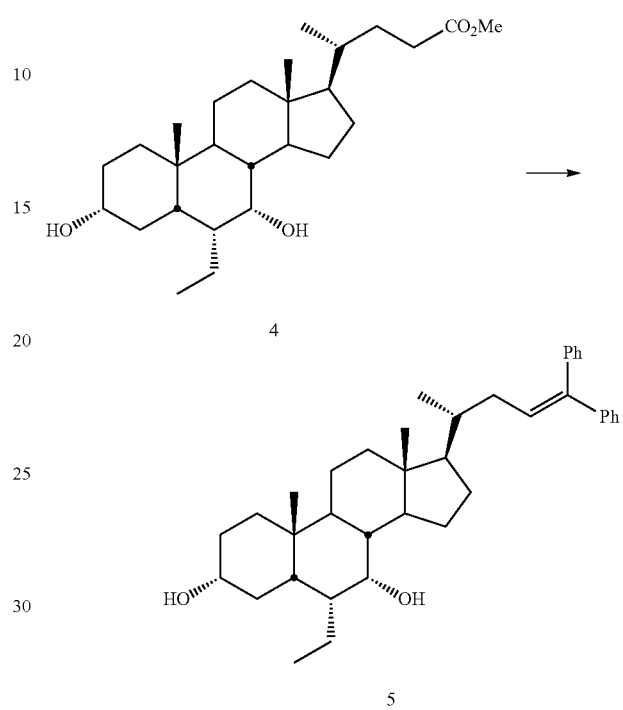

Compound 4 is dissolved in freshly distilled THF and the resulting mixture is warmed with stirring under a nitrogen atmosphere. Phenylmagnesiumbromide 1M in THF is added dropwise and the resulting mixture is stirred at the same temperature overnight. The reaction mixture is allowed to cool to room temperature and cyclohexane is added. The reaction mixture is filtered and the gum-solid residue is dissolved in a mixture of 3 N hydrochloric acid solution and DCM. The resulting mixture is stirred for 30 min. The organic phase is separated, and the aqueous phase is extracted with DCM. The combined organic layers are washed with brine, dried over $Na_2SO_4$, and the solvent is evaporated under vacuum. The crude residue is taken in DCM, washed with a saturated solution of sodium bicarbonate, water, brine, dried over anhydrous sodium sulfate and concentrated in-vacuo to afford Compound 5.

Example 6: Preparation of Compound 6

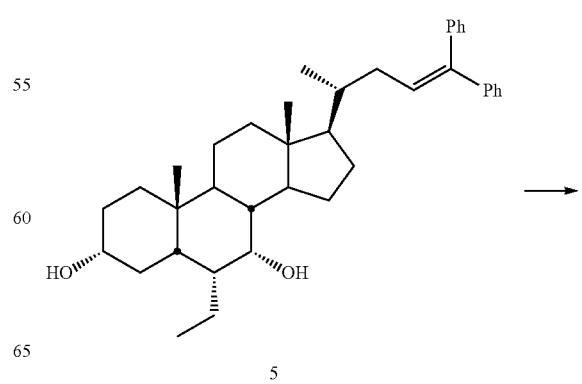

-continued

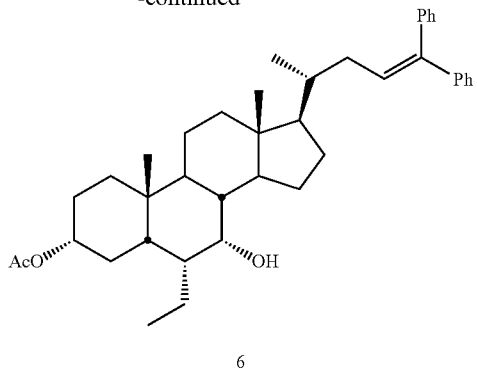

6

Acetic anhydride, pyridine, and 4-dimethylaminopyridine are added to a stirring solution of Compound 5 in freshly distilled THF. The reaction mixture is kept at room temperature overnight. The reaction mixture is diluted with water and extracted with DCM. The combined organic layers are washed with brine, dried over anhydrous sodium sulfate and the solvent is evaporated to afford Compound 6.

Example 7: Preparation of Compound 7

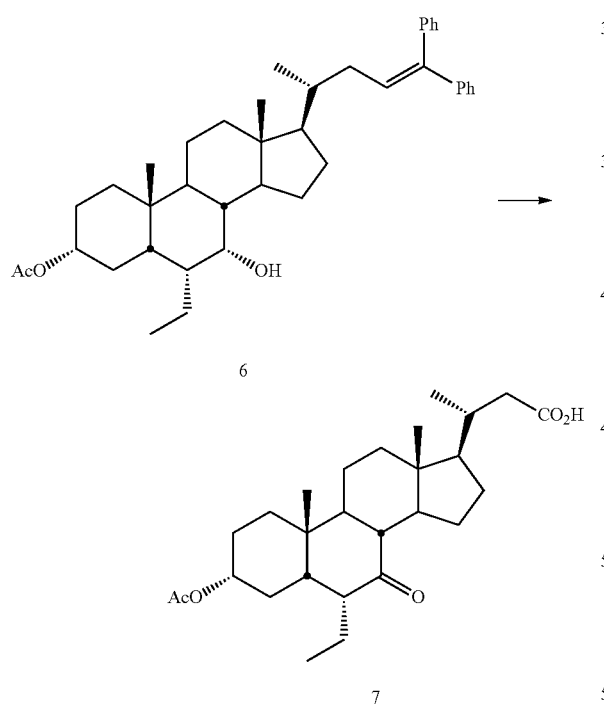

NaIO$_4$ is stirred in H$_2$O and 2N H$_2$SO$_4$. After 15 min, the reaction mixture is cooled to ° C. and RuCl$_3$ is added. The reaction mixture is stirred until the color turned into bright yellow. Ethyl acetate and acetonitrile are added and the resulting reaction mixture is stirred for 5 min. Compound 6 is added to the reaction mixture at 0° C., and stirred until Compound 6 is consumed. The reaction mixture is filtered, poured into H$_2$O and extracted with ethyl acetate. The combined organic layers are washed with a saturated solution of Na$_2$S$_2$O$_3$, dried over anhydrous Na$_2$SO$_4$ and concentrated under vacuum. The resulting residue is purified by flash chromatography to afford Compound 7 as a white solid.

Example 8: Preparation of Compound 8

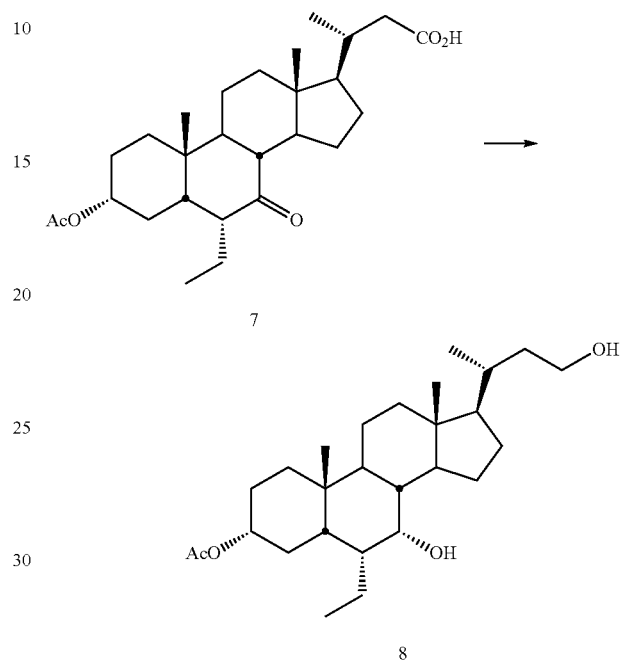

Triethylamine is added to a stirring ice-cooled solution of Compound 7 and isobutyl chloroformate in THF. After 1 hr, the reaction mixture is filtered under vacuum in an argon atmosphere. The resulting solution is treated with sodium borohydride for 1 hr at 0° C., which is added in portions. The reaction mixture is quenched with H$_2$O, stirred for additional 2 hr at room temperature, acidified with 3N hydrochloric acid and extracted with ethyl acetate. The combined organic extracts are washed with brine, dried over anhydrous Na$_2$SO$_4$, and concentrated under vacuum to afford Compound 8.

Example 9: Preparation of Compound 9 (Sodium Salt)

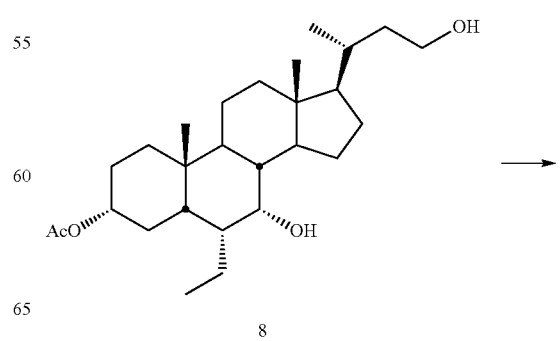

-continued

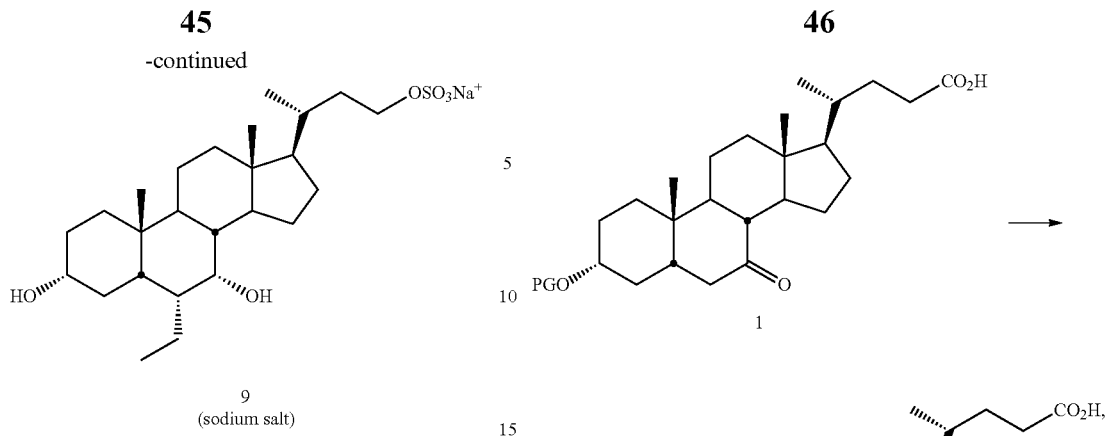

9
(sodium salt)

Compound 8 is added to a suspension of sulfur trioxide pyridine complex in dry pyridine (60 mL) and allowed to react at room temperature under nitrogen atmosphere for 24 hr. The solvent is evaporated, and the resulting residue is dissolved in methanol and treated with a 10% (w/w) solution of NaOH in MeOH. The reaction mixture is refluxed overnight. The solvent is evaporated and the resulting white solid is dissolved in a H$_2$O/MeOH solution and passed through a NaOH activated Dowex resin, eluting first with H$_2$O and then with a solution of H$_2$O/MeOH. The fractions containing the sodium salt of Compound 9 are evaporated to dryness and the resulting solid is purified via a reverse phase column RP-18 (Lobar C), using a H$_2$O/MeOH mixture as mobile phase.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A method of preparing obeticholic acid (OCA)

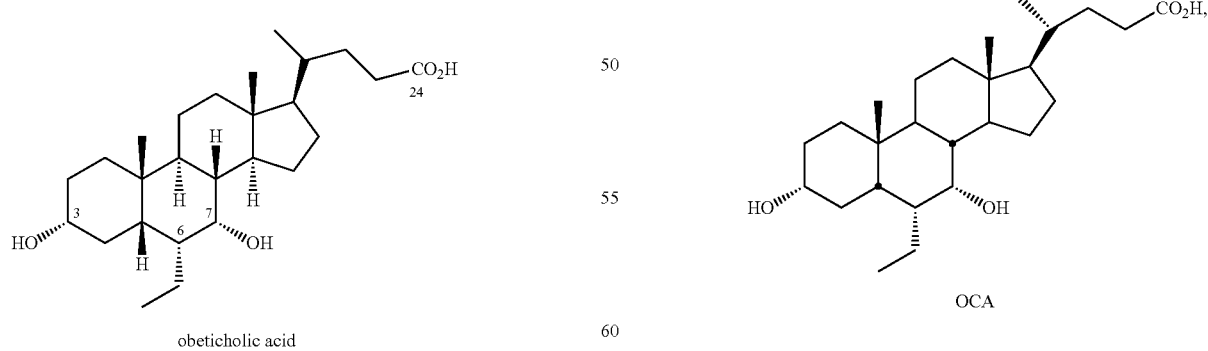

obeticholic acid or a pharmaceutical acceptable salt, solvate, or amino acid conjugate thereof, comprising:
   alkylating the carbon atom at the C-6 position of Compound 1 with an alkylating agent to form Compound 2:

wherein PG is a protecting group, and
   reducing the keto group at the C-7 position of Compound 2 to form OCA:

wherein the method is conducted at a temperature above −20° C.

2. The method of claim 1 wherein the alkylating agent is selected from alkyl halide, alkyl tosylate, alkyl mesylate, sulfonate ester, alkyl oxonium salt, dialkyl sulfate, dialkyl carbonate, and tetraalkylammonium salt.

3. The method of claim 2, wherein the alkylating agent is alkyl halide.

4. The method of claim 3, wherein the alkyl halide is ethyl bromide or ethyl iodide.

5. The method of claim 1, wherein the alkylation is conducted in an aprotic solvent selected from tetrahydrofuran (THF), ethyl acetate (EtOAc), acetone, dimethylformamide (DMF), acetonitrile (MeCN), dimethyl sulfoxide (DMSO), toluene, hexane, benzene, 1,4-dioxane, chloroform, dichloromethane (DCM), diethyl ether, and methyl tert-butyl ether (MTBE).

6. The method of claim 1, wherein the alkylation is conducted in the presence of a deprotonating agent selected from metal $C_1$-$C_6$ alkoxide, metal hydroxide, and metal hydride.

7. The method of claim 1 further comprising deprotonating Compound 1 before Compound 1 is alkylated.

8. The method of claim 1 further comprising deprotecting Compound 1 after alkylation of the carbon atom at the C-6 position.

9. The method of claim 1 further comprising protecting the hydroxyl group at the C-3 position of KLCA to form Compound 1:

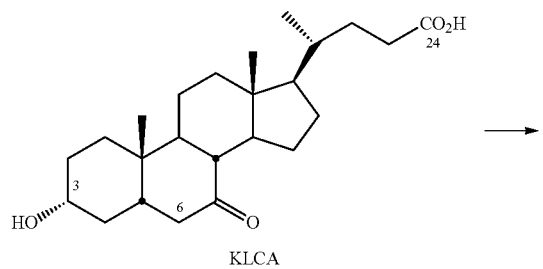

KLCA

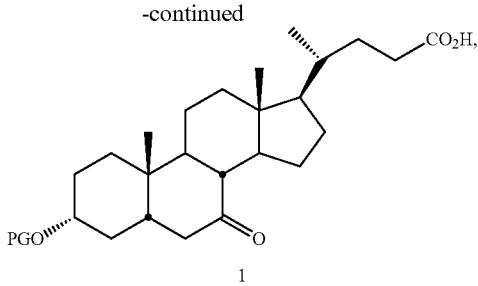

1 wherein PG is a protecting group.

10. The method of claim 9, wherein the protecting group is selected from acetyl, benzoyl, benzyl, pivaloyl, tetrahydropyranyl, tetrahydrofuranyl, 2-methoxyethoxymethyl ether (MEM), methoxymethyl ether (MOM), ethoxyethyl ether (EE), p-methoxybenzyl ether (PMB), methylthiomethyl ether, triphenylmethyl (trityl, or Tr), dimethoxytrityl (DMT), methoxytrityl (MMT), alkyloxycarbonyl, and silyl ether.

11. The method of claim 10, wherein the silyl ether is selected from trimethylsilyl ether (TMS), triethylsilyl ether (TES), triisopropylsilyl ether (TIPS), tert-butyldimethylsilyl ether (TBDMS), and tert-butyldiphenylsilyl ether (TBDPS).

12. The method of claim 9 further comprising protecting the carboxylic group at the C-24 position, wherein the protecting group of the hydroxyl group at the C-3 position is not tetrahydropyranyl or benzyl.

13. The method of claim 1, wherein the reduction comprises treating Compound 2 with a metal hydride.

14. The method of claim 1, wherein the method is conducted at a temperature between about $-10°$ C. to about $50°$ C.

15. The method of claim 6, wherein the deprotonating agent is metal $C_1$-$C_6$ alkoxide.

16. The method of claim 15, wherein the metal $C_1$-$C_6$ alkoxide is selected from potassium tert-butoxide, sodium tert-butoxide, sodium tert-pentoxide, and potassium tert-pentoxide.

* * * * *